(12) United States Patent
Shippert

(10) Patent No.: US 8,622,997 B2
(45) Date of Patent: Jan. 7, 2014

(54) TISSUE TRANSFER METHOD AND APPARATUS

(76) Inventor: Ronald D. Shippert, Littleton, CO (US)

( * ) Notice: Subject to any disclaimer, the term of this patent is extended or adjusted under 35 U.S.C. 154(b) by 625 days.

(21) Appl. No.: 12/484,781

(22) Filed: Jun. 15, 2009

(65) Prior Publication Data

US 2009/0287190 A1 Nov. 19, 2009

Related U.S. Application Data

(63) Continuation-in-part of application No. 12/046,300, filed on Mar. 11, 2008, which is a continuation-in-part of application No. 11/742,452, filed on Apr. 30, 2007, now Pat. No. 7,780,649, which is a continuation-in-part of application No. 11/553,920, filed on Oct. 27, 2006, now Pat. No. 7,789,872, which is a continuation-in-part of application No. 11/088,598, filed on Mar. 23, 2005, now Pat. No. 7,794,449.

(51) Int. Cl.
*A61M 1/00* (2006.01)

(52) U.S. Cl.
USPC .......... 604/542; 604/36; 604/37; 604/38; 604/121; 604/190; 604/218; 604/236; 604/237; 604/541

(58) Field of Classification Search
USPC ............................. 604/237, 541, 542
See application file for complete search history.

(56) References Cited

U.S. PATENT DOCUMENTS

| | | | |
|---|---|---|---|
| 1,138,764 A | 5/1915 | Kline | |
| 3,434,869 A * | 3/1969 | Davidson | 604/266 |
| 3,993,080 A | 11/1976 | Loseff | |
| 4,359,049 A | 11/1982 | Redl et al. | |
| 4,447,230 A * | 5/1984 | Gula et al. | 604/122 |
| 4,548,207 A | 10/1985 | Reimels | |
| 4,683,884 A | 8/1987 | Hatfield et al. | |
| 4,753,634 A | 6/1988 | Johnson | |
| 4,770,187 A | 9/1988 | Lash et al. | |
| D298,650 S | 11/1988 | Lash | |
| 4,834,703 A | 5/1989 | Dubrul et al. | |
| 4,883,755 A | 11/1989 | Carabasi et al. | |
| 4,957,492 A * | 9/1990 | McVay | 604/319 |
| 5,035,708 A | 7/1991 | Alchas | |
| 5,049,146 A | 9/1991 | Bringham et al. | |
| 5,052,999 A | 10/1991 | Klein | |

(Continued)

FOREIGN PATENT DOCUMENTS

| | | |
|---|---|---|
| EP | 1531881 | 5/2005 |
| EP | 1531882 | 5/2005 |

(Continued)

OTHER PUBLICATIONS

LipiVage, product insert, 2 pages, Aug. 2004.

(Continued)

*Primary Examiner* — Tatyana Zalukaeva
*Assistant Examiner* — Ilya Treyger
(74) *Attorney, Agent, or Firm* — Sheridan Ross P.C.

(57) ABSTRACT

A system in accordance with embodiments of the present invention includes a cannula interconnected to a collection vessel by a flexible conduit. The collection vessel can comprise an impermeable or permeable collection vessel. The collection vessel is contained within a collection container, and can feature a tapered end. An air inlet may be provided in the flexible conduit and/or in a collection canister lid.

15 Claims, 26 Drawing Sheets

(56) References Cited

U.S. PATENT DOCUMENTS

| | | |
|---|---|---|
| 5,312,380 A | 5/1994 | Alchas et al. |
| 5,338,294 A | 8/1994 | Blake, III |
| 5,352,194 A | 10/1994 | Greco et al. |
| 5,352,410 A | 10/1994 | Hansen et al. |
| 5,372,945 A | 12/1994 | Alchas et al. |
| 5,441,539 A | 8/1995 | Alchas et al. |
| 5,569,178 A | 10/1996 | Henley |
| 5,603,845 A | 2/1997 | Holm |
| 5,766,134 A | 6/1998 | Lisak et al. |
| 5,786,207 A | 7/1998 | Katz et al. |
| 5,804,366 A | 9/1998 | Hu et al. |
| 5,827,217 A | 10/1998 | Silver et al. |
| 5,911,700 A | 6/1999 | Mozsary et al. |
| 5,976,470 A | 11/1999 | Maiefski et al. |
| 6,013,048 A | 1/2000 | Podany et al. |
| 6,024,725 A | 2/2000 | Bollinger et al. |
| 6,258,054 B1 | 7/2001 | Mozsary et al. |
| 6,299,763 B1 | 10/2001 | Ashman |
| 6,303,286 B1 | 10/2001 | Dennis et al. |
| 6,315,756 B1 | 11/2001 | Tankovich |
| 6,316,247 B1 | 11/2001 | Katz et al. |
| 6,468,225 B1 | 10/2002 | Lundgren |
| 6,494,876 B1 | 12/2002 | Fowler et al. |
| 6,623,733 B1 | 9/2003 | Hossainy et al. |
| 6,626,890 B2 | 9/2003 | Nguyen et al. |
| 6,777,234 B1 | 8/2004 | Dennis et al. |
| 7,097,690 B2 | 8/2006 | Usher et al. |
| 7,335,513 B2 | 2/2008 | Smith |
| 7,390,484 B2 | 6/2008 | Fraser et al. |
| 7,687,059 B2 | 3/2010 | Fraser et al. |
| 2002/0146817 A1 | 10/2002 | Cannon et al. |
| 2002/0198474 A1 | 12/2002 | Becker |
| 2003/0161816 A1 | 8/2003 | Fraser et al. |
| 2003/0162707 A1 | 8/2003 | Fraser et al. |
| 2004/0067219 A1 | 4/2004 | Vida |
| 2004/0097867 A1 | 5/2004 | Fraser et al. |
| 2004/0106196 A1 | 6/2004 | Fraser et al. |
| 2005/0025755 A1 | 2/2005 | Hendrick |
| 2005/0084961 A1 | 4/2005 | Hendrick et al. |
| 2005/0186671 A1 | 8/2005 | Cannon et al. |
| 2006/0093527 A1 | 5/2006 | Buss |
| 2006/0213374 A1 | 9/2006 | Shippert |
| 2006/0258004 A1 | 11/2006 | Kosnik et al. |
| 2007/0100277 A1 | 5/2007 | Shippert |
| 2007/0225686 A1 | 9/2007 | Shippert |
| 2008/0014181 A1 | 1/2008 | Ariff et al. |
| 2008/0058763 A1 | 3/2008 | Boland et al. |
| 2008/0154240 A1 | 6/2008 | Shippert |
| 2009/0192454 A1 | 7/2009 | Boland et al. |

FOREIGN PATENT DOCUMENTS

| | | |
|---|---|---|
| EP | 1921133 | 5/2008 |
| WO | WO 00/77164 | 12/2000 |
| WO | WO 2004/067065 | 8/2004 |
| WO | WO 2005/011569 | 2/2005 |
| WO | WO 2005/012480 | 2/2005 |
| WO | WO 2005/034843 | 4/2005 |
| WO | WO 2005/095581 | 10/2005 |
| WO | WO 2006/014156 | 2/2006 |
| WO | WO 2006/014159 | 2/2006 |
| WO | WO 2006/022612 | 3/2006 |
| WO | WO 2006/026969 | 3/2006 |
| WO | WO 2006/127007 | 11/2006 |
| WO | WO 2008/137234 | 11/2008 |
| WO | WO 2009/149691 | 12/2009 |

OTHER PUBLICATIONS

Genesis Biosystems, Advancing the Science of Skincare, LipiVage, 1 page, at http://www.dermagenesis.com/prodlipivage.cfm, printed Oct. 25, 2004.

Genesis Biosystems, Advancing the Science of Skincare, LipiVage, 3 pages, at http://www.dermagenesis.com/prodlipivage.cfm, printed Mar. 16, 2005.

LipiVage Fat Harvest, Wash & Transfer System, available at www.lipivage.com, Genesis Biosystems, Inc., 2 pages, printed Sep. 21, 2005.

Lee W. Young, Written Opinion for International (PCT) Patent Application No. PCT/US08/59469, mailed Aug. 28, 2008, pp. 1-5.

Lee W. Young, International Search Report for International (PCT) Patent Application No. PCT/US 08/59469, mailed Aug. 28, 2008, pp. 1-3.

Restriction Requirement for U.S. Appl. No. 11/088,598, filed Mar. 23, 2005, mailed Feb. 12, 2009, pp. 1-5.

Restriction Requirement for U.S. Appl. No. 11/553,920, filed Oct. 27, 2006, mailed Feb. 12, 2009, pp. 1-5.

Restriction Requirement for U.S. Appl. No. 11/742,452, filed Apr. 30, 2007, mailed Feb. 20, 2009, pp. 1-5.

Office Action for U.S. Appl. No. 11/742,452, filed Apr. 30, 2007, mailed May 12, 2009, pp. 1-7.

Office Action for U.S. Appl. No. 11/553,921, mailed Jul. 7, 2009, pp. 1-11.

Office Action for U.S. Appl. No. 11/088,598, mailed Jul. 21, 2009, pp. 1-15.

Final Office Action for U.S. Appl. No. 11/742,452, mailed Nov. 6, 2009, 10 pages.

Interview Summary for U.S. Appl. No. 11/742,452, mailed Dec. 16, 2009, pp. 1-3.

Final Office Action for U.S. Appl. No. 11/088,598, mailed Mar. 3, 2010, pp. 1-17.

Final Office Action for U.S. Appl. No. 11/553,920, mailed Mar. 26, 2010, pp. 1-11.

U.S. Appl. No. 12/434,073, filed May 1, 2009, patent application and figures as filed.

Notice of Allowance for U.S. Appl. No. 11/742,452, mailed Jan. 4, 2010, 4 pages.

Interview Summary for U.S. Appl. No. 11/088,598, mailed May 19, 2010, 3 pages.

Notice of Allowance and Fee(s) Due for U.S. Appl. No. 11/088,598, mailed Jun. 10, 2010, 8 pages.

Interview Summary for U.S. Appl. No. 11/553,920, mailed May 19, 2010, 4 pages.

Notice of Allowance and Fee(s) Due for U.S. Appl. No. 11/553,920, mailed Jun. 10, 2010, 8 pages.

U.S. Appl. No. 13/174,169, filed Jun. 30, 2011, Shippert.

Restriction Requirement for U.S. Appl. No. 12/046,300, mailed Aug. 30, 2010, 6 pages.

Official Action for U.S. Appl. No. 12/046,300, mailed Oct. 13, 2010, 33 pages.

Official Action for U.S. Appl. No. 12/046,300, mailed Mar. 22, 2011, 7 pages.

Notice of Allowance for U.S. Appl. No. 12/046,300, mailed Sep. 20, 2011, 6 pages.

* cited by examiner

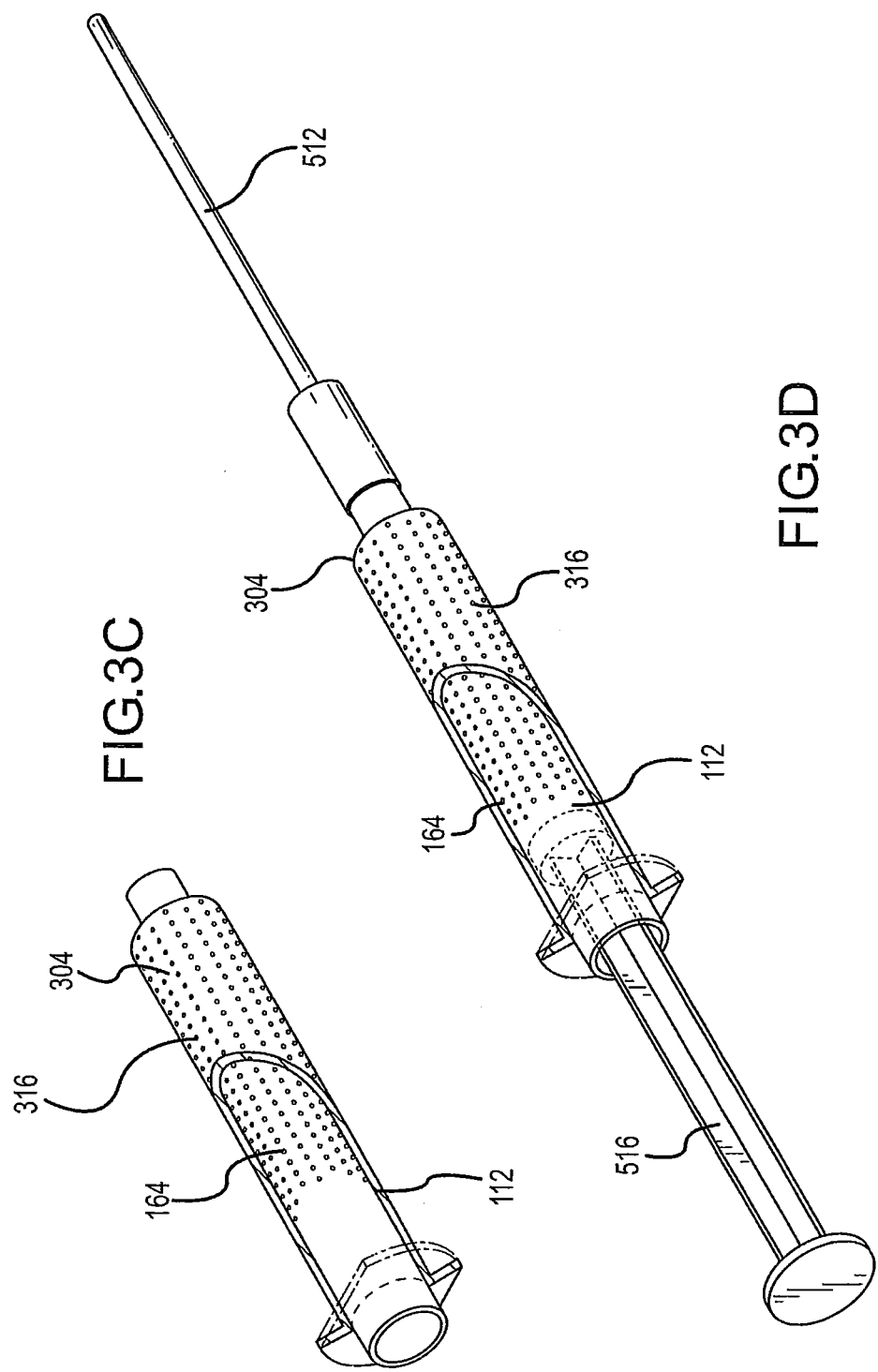

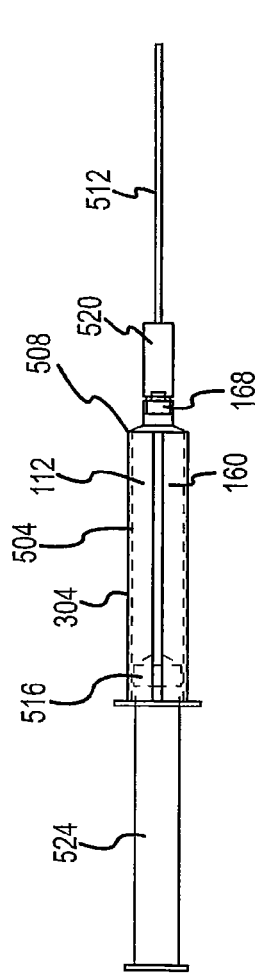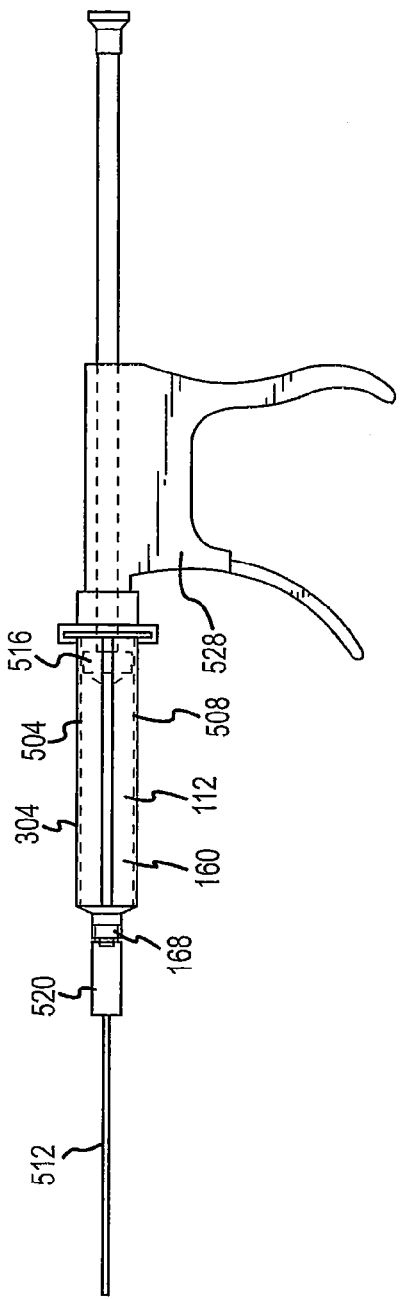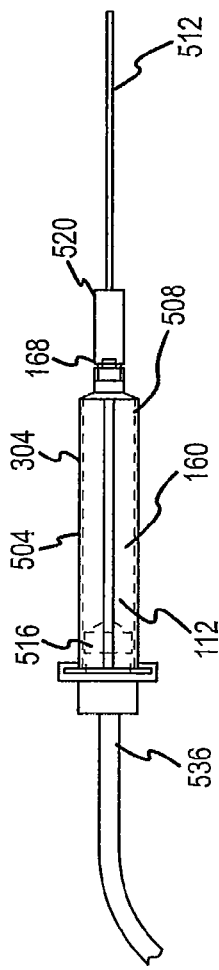

TISSUE TRANSFER METHOD AND APPARATUS

CROSS-REFERENCE TO RELATED APPLICATIONS

This application is a Continuation-In-Part of application Ser. No. 12/046,300, filed Mar. 11, 2008, which is a Continuation-In-Part of application Ser. No. 11/742,452, filed Apr. 30, 2007, which is a Continuation-In-Part of application Ser. No. 11/553,920, filed Oct. 27, 2006, which is a Continuation-In-Part of application Ser. No. 11/088,598, filed Mar. 23, 2005, the entire disclosures of which are hereby incorporated herein by reference.

FIELD

The present invention is directed to the transplantation of tissue in bodies.

BACKGROUND

Microlipoinjection is a process in which fat is taken by a cannula from one spot in the body and reinjected in another place in the body. Microlipoinjection has also been known as liposuction with fat transfer or fat transplantation. In general, microlipoinjection is performed to treat divots and scar indentations from trauma to the face or body, such as may occur as a secondary effect of domestic trauma, surgery or infection. Microlipoinjection can also be used to treat the effects of the loss of the subcutaneous layer of fat due to the normal aging process, either alone or in combination with facelift and fat grafting techniques. Microlipoinjection can also be used for providing filler to reapproximate weakened vocal cords, fill sinuses, or partially close incompetent valves.

Up to about 1990, there were few artificial filler substances available to surgeons. Accordingly, surgeons used human bone, collagen and fat as fillers. However, the use of fat was not very successful, because the instruments and techniques were not sufficiently refined. For example, 50% of the fat may not have lived through the transplantation process. As a result, surgeons would need to implant more fat than would be required if all of the fat survived the process, or the transplantation process would have to be repeated multiple times.

More recently, a number of filler substances, such as Restylane Hyaluronic Acid, Collagen, Fibril, ePTFE (Teflon®), Hylan B Gel, Artecol, BioBlastique and have been used. These substances have proved effective at filling small areas, but the cost for larger areas has become prohibitive. For this reason, as well as interest in the "natural substance" concept, surgeons and their patients have again looked at using fat as a filler.

With the renewed interest in using fat as a filler, techniques have been refined to provide a better fat graft "take" with revascularization. However, the instruments and devices conventionally available to perform the procedure remain clumsy and ill-suited for the procedure. As a result, the procedure has remained difficult to perform, cumbersome, time consuming, expensive and relatively unsuccessful. For example, the conventional process employed in connection with microlipoinjection comprises about 10 steps, some of which can cause damage to a significant percentage of the fat cells. In addition, it is necessary to maintain strict sterility throughout all of the steps. However, sterility is difficult to maintain in connection with centrifuging, which is performed separately from the sterile operating field, and involves ancillary personnel. The basic steps of the conventional microlipoinjection process can be summarized as follows:

Step 1—Liposuction of fat from the donor area, the fat going into a large syringe or canister. The suction aspirate contains the wanted fat, plus the unwanted blood, serum, anesthetic agent, etc. These later substances must be removed for the best lipocyte survival rates.

Step 2—Fat is transferred into several smaller syringes that will fit into a centrifuge. Every time the fat is transferred to another syringe, there is more destruction of fat cells secondary to pressure of the plunger forcing the fat through the narrow outlet of the syringe into the input luer of the next syringe. Caps are placed on the end of the syringe to prevent loss during centrifuging.

Step 3—Centrifuge for several minutes or until the contents are in three layers: the top layer is triglyceride oils, the middle layer is fat, and the lower layer is the remaining blood cell debris.

Step 4—Decant off the top liquid oil and serum from the centrifuge specimen.

Step 5—Place the plunger in the syringe, tip syringe upward and squirt out the red cells and debris, leaving the residual fat in the syringe. Sometimes this has to be repeated, including repeat centrifuging, a number of times for proper separation.

Step 6—Treat contents with irrigation solutions, platelet rich plasma (PRP), albumin, growth hormone, or other substances, by aspirating this substance into the syringe. These substances are considered helpful in ensuring the viability of the lipocyte (fat cell). Some of these substances aid in angiogenesis (establishment of blood vessels) or treat in a manner that encourages lipocyte survival.

Step 7—Gently mix by circular motion.

Step 8—Centrifuge again.

Step 9—Decant off liquid additive.

Step 10—Put the plunger back into the syringe, place an injection needle on the tip and inject the fat into the divot or wrinkle. This injection is conventionally done manually with a control syringe or special manual mechanical gun.

The washing and/or treatment of tissue, for example to remove broken fat cell walls and contents, to remove chemicals introduced during the tissue removal process, and to treat the removed tissue, is often desirable. However, the washing and/or treatment of tissue comprising fat using irrigation solutions is particularly problematic, because conventional techniques for treating or washing the tissue often result in traumatic events for the tissue cells and increase the chance of microbe contamination. In particular, conventional washing techniques have been time-consuming and expose the tissue to the hands of the surgical staff, exposes the tissue to the ambient air, and passes the tissue through different devices. This is because of the techniques involved: first removing the tissue from the body; placing the removed tissue into a wash container; manually mixing sterile solution with the tissue; stirring the mixture; filtering it; centrifuging it; and then transferring it to the appropriate syringe for reinjection. Accordingly, it would be desirable to reduce the time required to rid the specimen of unwanted, broken fat cell walls, broken fat cell contents, as well as chemicals that have been introduced for anesthesia and vasoconstriction and/or to otherwise treat the removed tissue. In addition, it would be desirable to reduce the trauma to cells of removed tissue, and to reduce the chance of contamination of such tissue.

SUMMARY

Embodiments of the present invention are directed to solving these and other problems and disadvantages of the prior art. In accordance with embodiments of the present invention, a tissue collection vessel is provided for receiving tissue removed from a donor site. More particularly, the tissue collection vessel may receive tissue removed from a donor site within a human or animal body using a cannula connected to a vacuum source. The collection vessel may be intermediate to the cannula and the vacuum source. In addition, the collection vessel may be placed within a canister, and a vacuum may be created within the canister.

In accordance with other embodiments of the present invention, the collection vessel may comprise an impermeable vessel disposed within a tissue collection canister. Moreover, the tissue collection vessel can comprise a flexible or semi-rigid bag. The tissue collection vessel may include an inlet in communication with a cannula, for receiving tissue removed from a body. The tissue collection vessel may also include a vacuum outlet. The tissue collection vessel may be placed within a canister in which a vacuum is formed in order to hold the tissue collection vessel open to facilitate the receipt of removed tissue into the interior of the tissue collection vessel. In accordance with still other embodiments of the present invention, a filter may be provided within the tissue collection vessel to promote the separation of desired tissue from additives and other fluids.

In accordance with embodiments of the present invention in which the collection vessel comprises a removable collection bag, desired tissue, such as fat, can be separated from additives or other fluids by turning the bag upside down, such that at least one port of the bag is below the contents of the bag, and opening the port to allow fluids to escape. The remaining tissue can then be removed from the bag, and placed in one or more syringe bodies for reinjection, or in another vessel for storage. The use of a collection bag also allows collected tissue to be washed and/or instilled with an additive by placing additional fluid into the collection bag with desired tissue, and then massaging the exterior of the collection bag to mix the additive and collected tissue.

In accordance with still other embodiments of the present invention, a device for collecting tissue comprising a collection bag can be used in combination with a device for collecting tissue comprising one or more syringe bodies. In particular, removed tissue can initially be collected, and if desired treated, in a collection bag. The collected tissue can then be transferred to syringe bodies. Accordingly, tissue can be prepared for reinjection and placed into a syringe body that will be used for reinjection, without requiring manual handling of the tissue.

In accordance with other embodiments of the present invention, the tissue collection vessel comprises a porous inner bag that functions as a filter. The tissue collection vessel or filter in such embodiments may be disposed within a tissue collection canister. In addition, a vacuum outlet may be interconnected to a waste tube that extends to the bottom or end of the tissue collection canister that is generally opposite the inlet to the tissue collection vessel. The tissue collection vessel can feature a tapered end proximate to the inlet to the tissue collection vessel. By providing a tapered end, the removal of tissue from the bag, for example for placement into a syringe for reinjection, can be facilitated. A tapered end may be provided in both permeable and impermeable embodiments of the tissue collection vessel.

In accordance with further embodiments, a tissue collection system with an air inlet is provided. In particular, the air inlet is in addition to a tissue collection inlet of a tissue collection cannula. The air inlet can be provided in tubing interconnecting the tissue collection cannula to the tissue collection vessel, in the tissue collection canister, or in the lid of the tissue collection canister. In accordance with still other embodiments, multiple air inlets may be provided.

Additional features and advantages of embodiments of the present invention will become more readily apparent from the following discussion, particularly when taken together with the accompanying drawings.

BRIEF DESCRIPTION OF THE DRAWINGS

FIGS. 3C-3D are views of a perforated chamber and perforated sleeve in accordance with other embodiments of the present invention;

FIGS. 5A-5C are side elevations of an inner chamber configured for the reinjection of tissue in connection with exemplary reinjection apparatuses, in accordance with embodiments of the present invention;

DETAILED DESCRIPTION

Figure 1:
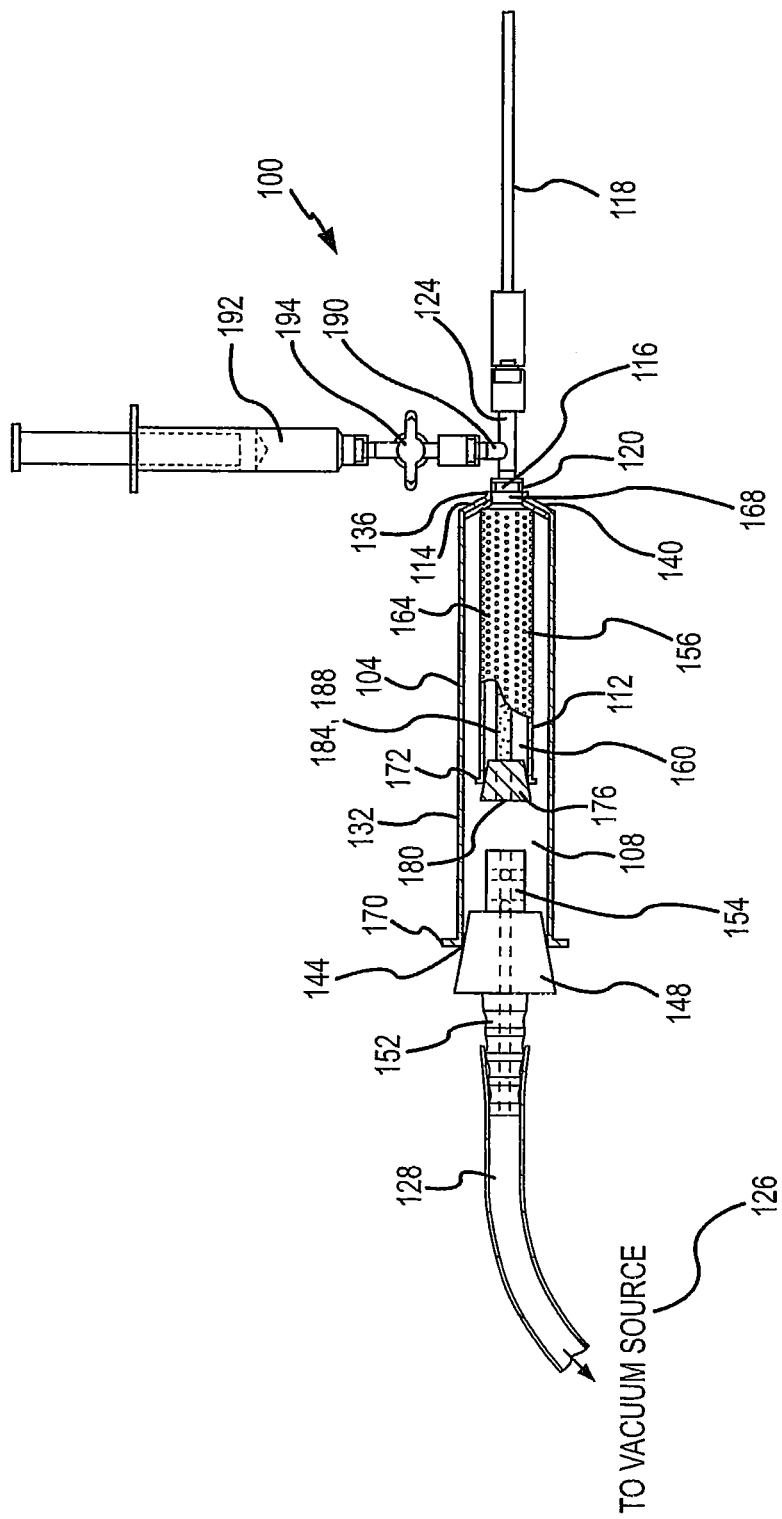
FIG. 1 is a cross-section of a device for tissue transplantation in accordance with embodiments of the present invention.

With reference now to FIG. 1, a tissue transplantation device 100 in accordance with embodiments of the present invention is depicted in cross-section. In general, the device 100 includes an outer chamber 104 defining an interior volume 108 sized to accommodate a perforated inner chamber 112. The device 100 additionally includes a cannula or needle 118 interconnected to an inlet 120 of the inner chamber 112, either directly or through an intermediate conduit 124. The interior volume 108 of the outer chamber 104 is placed in communication with a vacuum source 126 via a suction or vacuum line 128.

In accordance with embodiments of the present invention, the outer chamber 104 includes a substantially rigid body portion 132. As used herein, in connection with at least the outer chamber body 132, substantially rigid means that the outer chamber body 132 is capable of maintaining the interior volume 108 while a vacuum is established within the interior volume 108. For example, the outer chamber body 132 may be capable of maintaining the interior volume 108 while a vacuum of about 10 to 30 inches of mercury is established in the interior volume 108. Accordingly, the interior volume 108 can be operative as a vacuum chamber. In accordance with further embodiments of the present invention, the outer chamber body 132 may be rigid enough to allow a surgeon to use the outer chamber 104 as a handle while manipulating an attached or interconnected cannula 118 in connection with the removal of tissue from a donor site. In accordance with still further embodiments of the present invention, the outer chamber body 132 may be formed from a transparent or semitransparent material, to allow the perforated inner chamber 112 within the interior volume 108 to be viewed. In addition, the outer chamber body 132 of embodiments of the present invention such as illustrated in FIG. 1 may be generally cylindrical, and the interior volume 108 may comprise a generally cylindrical bore.

At a distal end 114, the outer chamber 104 may include an inlet 136 adapted to receive an inlet 168 of the inner chamber 112. Furthermore, in accordance with embodiments of the present invention, the inlet 136 may comprise a hole having a diameter such that it can receive the distal end 116 of the perforated inner chamber 112 in close fitting contact. A gasket 140 may also be provided at the distal end of the outer chamber 104 to assist in preventing vacuum leaks at the interface between the outer chamber inlet 136 and the inner chamber inlet 168.

The outer chamber 104 may additionally feature an open proximal end 144. During the aspiration of tissue, the proximal end 144 of the outer chamber 104 may receive a tapered plug 148. The plug 148 seals the open end 144 of the outer chamber 104, and may provide a tube 152 comprising a nipple, tapered stub or other fitting to which the suction tubing 128 can be interconnected, thereby permitting the interior volume 108 of the outer chamber 104 to be interconnected to a vacuum source 126. The tube 152 may optionally comprise or be associated with an end plug filter 154 to prevent some or all of the material drawn off of collected fat tissue from passing to the suction tube 128 and the vacuum source 126. Alternatively or in addition, filters may also be provided between the end plug 148 and the vacuum source 126. If provided, a filter 154 or other filter may comprise various filter arrangements and media, including perforated tubes, absorbent foams and gauzes, cartridges containing particulate filtration media, and/or other filtration media and structures. In accordance with further embodiments of the present invention, the tapered plug 148 may be removable, to permit access to the interior volume 108 of the outer chamber 104. In accordance with embodiments of the present invention, the tapered plug 148 may comprise a silicone or rubber material, with a tube 152 formed from metal or a polymer. Furthermore, it should be appreciated that the plug 148 need not be tapered. For example, the plug 148 can comprise a cap or an insert having threads that can interconnect with mating threads on the outer chamber body 132, the plug 148 can have a constant diameter for fitting in or over a mating surface formed as part of the outer chamber body 132, or can be formed in some other way to seal the proximal end 144 of the outer chamber 104.

The inner chamber 112 includes a substantially cylindrical body portion 156 having a substantially cylindrical interior bore 160. More particularly, the inner chamber body portion 156 is substantially cylindrical in that it does not feature projections, so that an inner chamber sleeve 304 (see FIGS. 3A-3D) can be accommodated, as will be described in greater detail elsewhere herein. Furthermore, the body portion 156 may be substantially rigid. As used herein in connection with at least the inner chamber body portion 156, substantially rigid means the cylindrical body portion 156 maintains its shape while tissue is collected within the interior bore 160 and while collected tissue is being forced from the interior bore 160. Furthermore, because the body portion 156 is substantially rigid, it can function as the body of a syringe, as described in greater detail elsewhere herein. In addition, a plurality of perforations 164 are formed in the cylindrical body 156. At the distal end 116 of the inner chamber 112, an inlet 168 is provided. The inlet 168 may provide surfaces for being received by the inlet 136 of the outer chamber 104 and/or the gasket 140, so that a seal is maintained at the interface between the outer chamber inlet 136 and the distal end of the inner chamber 112. In addition, the fitting between the outer chamber inlet 136 and the inlet 168 of the inner chamber 112 can secure the inner chamber 112 with respect to the outer chamber 104 while tissue is being aspirated from a donor site. Accordingly, the interface between the inlet 136 of the outer chamber 104 and the inlet 168 of the inner chamber 112 may comprise a friction fitting, or a mechanical lock, such as may be provided by cooperating threads or other mechanical arrangement. In addition, the inlet 168 of the inner chamber 112 may provide a fitting for receiving a cannula or needle 118, and/or an intermediate conduit 124. Accordingly, exemplary embodiments of an inner chamber 112 may comprise an inlet 168 that provides the male portion of a luer connector. In accordance with embodiments of the present invention, no protrusions or flanges extend from the area of the body portion 156 and/or the area of the interior bore 160 in which the perforations 164 are formed. However, a flange or handle 170 may be provided, for example to assist in using the inner chamber 112 as the body of a syringe, as described herein.

The inner chamber body 156 may include an open proximal end 172. During the aspiration of tissue, the proximal end 172 may be sealed by a plug 176. In accordance with embodiments of the present invention, the plug 176 may have a center bore 180 that can house either an absorbent stick 184 or a perforated central suction tube 188. Where an absorbent stick 184 is provided, the stick may be formed from a compressed stick of polyvinyl alcohol (PVA) foam to aid in the absorption of residual oils from collected fat. In accordance with embodiments of the present invention, the stick is disposed of after use. The absorbent stick 184 may extend into the interior volume of the inner chamber 112, for example to almost the inlet 168 at the distal end 116 of the inner chamber 112. In connection with embodiments where a perforated central suction tube 188 is provided, suction created by placing the interior volume 108 of the outer chamber 104 in communication with a vacuum source can be used to draw material from collected fat from the center of the collected fat specimen. The perforations 190 in the central suction tube 188 may be sized and arranged like the perforations 164 in the inner chamber 112 body 156. The central suction tube 188 may extend almost to the inlet 168 at the distal end 116 of the inner chamber 112. An absorbent stick 184 may also be combined with a suction tube. In accordance with embodiments of the present invention, the plug 176 may be formed from a polymer and may be tapered to seal the open end 172 of the inner syringe 112. Alternatively, the plug 148 may be threaded to interconnect to mating threads provided as part of the inner chamber 112, or to interconnect and seal the proximal end of inner chamber 112 through some other arrangement.

Embodiments of the present invention may provide an intermediate conduit 124 for interconnecting the cannula 118 to the inlet 168 of the inner chamber 112. As used herein, the term cannula may include needles. Specifically, a needle is a particular type of cannula, in that it refers to a relatively small cannula. Furthermore, the conduit 124 may comprise an inlet branch 190 for selectively interconnecting a fluid reservoir 192 to the conduit 124 through a stopcock 194. Accordingly, embodiments of the present invention may allow a fluid, for example an additive or tissue treatment fluid, to be introduced or instilled in tissue as that tissue is collected and drawn through the conduit 124 to the inner chamber 112. In accordance with embodiments of the present invention, the fluid reservoir 192 can comprise a syringe.

As can be appreciated by one of skill in the art from the description provided herein, when operatively assembled and configured for the removal of tissue from a donor site, a device 100 allows tissue to be aspirated through a cannula 118 by interconnecting the device 100 to a vacuum source 126. Tissue collected through the cannula 118 is passed through a conduit 124, if provided, and into the interior bore 160 of the inner chamber 112. In accordance with embodiments of the present invention, the inner canal of the cannula 118, a conduit 124, and the inlet 168 of the inner chamber 112 are substantially uniform and as large as mechanical feasible. Such an arrangement helps to prevent the damage that can be caused by forcing aspirated fat through narrow conduits and changes in conduit size.

The fat drawn into the interior bore 160 of the inner chamber 112 is collected in the inner chamber 112, while blood, serum, anesthetic agents and/or other materials are drawn through the perforations 164, and into the interior volume 108 of the outer chamber 104 by the vacuum introduced through the tube 152. The materials drawn off of the fat may additionally include additive introduced from a reservoir 192 to the flow of tissue through the conduit 124, or drawn into the inner chamber 112 from a reservoir 192 after tissue has been collected in the inner chamber 112. The materials drawn off of the collected fat may be collected by filters, for example in-line with the vacuum line 128 or provided as part of the vacuum source 126, to prevent such material from reaching the pump mechanism of the vacuum source 126. Accordingly, separation of collected fat from other, unwanted materials, can be effected without removing the collected fat from the inner chamber 112. In addition, separation of the collected fat from other materials can be effected without requiring centrifuging.

Figure 2:
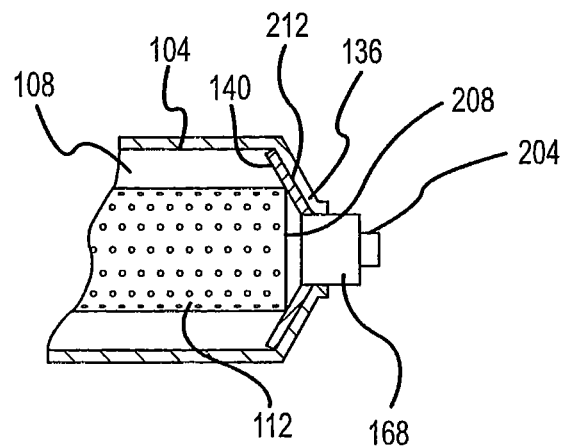
FIG. 2 is a partial cross-section of components of a device for tissue transplantation in accordance with embodiments of the present invention.

With reference now to FIG. 2, a detail of the relationship between the inlet 136 of the outer chamber 104 and the inlet 168 of the inner chamber 112 is shown. In particular, it can be seen that the inlet 168 of the inner chamber 112 may, in accordance with embodiments of the present invention, comprise the male portion of a slip type luer connector 204. According to other embodiments, the inlet 168 can comprise a lock type luer connector or other fitting. In addition, it can be seen that the inlet 168 may include a barrel portion, for example as part of the luer connector 204, that is in close fitting contact with the opening of the outer chamber inlet 136, when the inner chamber 112 is inserted into the interior volume 108 of the outer chamber 104 such that the inlet 168 of the inner chamber 112 protrudes from the inlet 136 of the outer chamber 104. FIG. 2 also shows that the distal end 116 of the inner chamber 112 may include a tapered or dished surface 208 having an angle that is equal or complementary to a tapered surface 212 at the distal end 114 of the outer chamber 104, and that the tapered surfaces 208, 212 can hold the gasket 140 between them, to form a seal between the inlet 168 of the inner chamber 112 and the inlet 136 of the outer chamber 104.

Figure 3A:
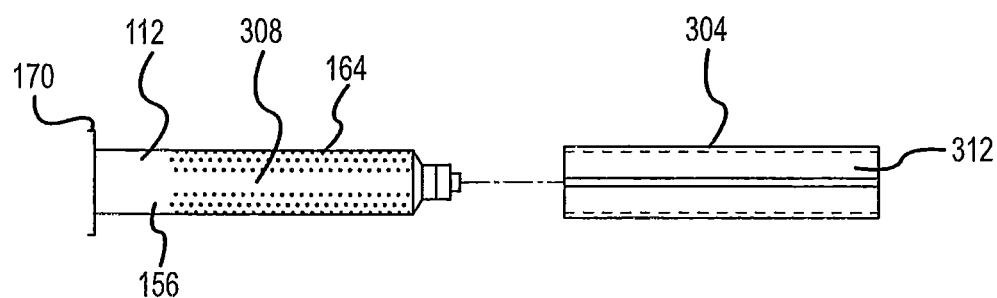
FIGS. 3A-3B are views of a perforated chamber and sleeve in accordance with embodiments of the present invention.

With reference now to FIG. 3A, an inner chamber 112 in accordance with embodiments of the present invention is illustrated. In addition, an inner chamber sleeve 304 is shown. In accordance with embodiments of the present invention, the perforations 164 in the body portion 156 of the inner chamber 112 do not extend along at least a first area or portion 308 of the inner chamber body 156. In addition, the inner chamber sleeve 304 may include a slit 312. Accordingly, the inner chamber sleeve 304 may be formed so that it has a diameter that is slightly smaller than the outside diameter of the body 156 of the inner chamber 112. Therefore, when the inner chamber sleeve 304 is slipped over the body 156 of the inner chamber 112, it can tightly cover the perforations 164, and the slit 312 can be registered with the portion 308 along which no perforations 164 are formed. As can be appreciated by one of skill in the art after appreciation of the disclosure provided herein, the inner chamber sleeve 304 may be positioned to cover the perforations 164 in the inner chamber 112 when the inner chamber 112 has been removed from the outer chamber interior volume 108, in preparation for the reinjection of collected tissue. In accordance with other embodiments of the present invention, the inner chamber sleeve 304 may be sized so that it can be received within the interior bore of the inner chamber 112 to close off the perforations 164 from the inside of the inner chamber 112. Furthermore, embodiments of the present invention do not require that a slit 312 be formed in the inner chamber sleeve 304. For example, the perforations 164 can be covered using a cylindrical inner chamber sleeve 304 that does not have a slit and that is dimensioned to fit tightly over the outside of the inner chamber 112. Moreover, the inner chamber sleeve 304 can be formed from a silicone tube having an inner diameter that is smaller than the outer diameter of the inner chamber 112, and a length that is sufficient to cover all of the perforations 164.

Figure 3B:
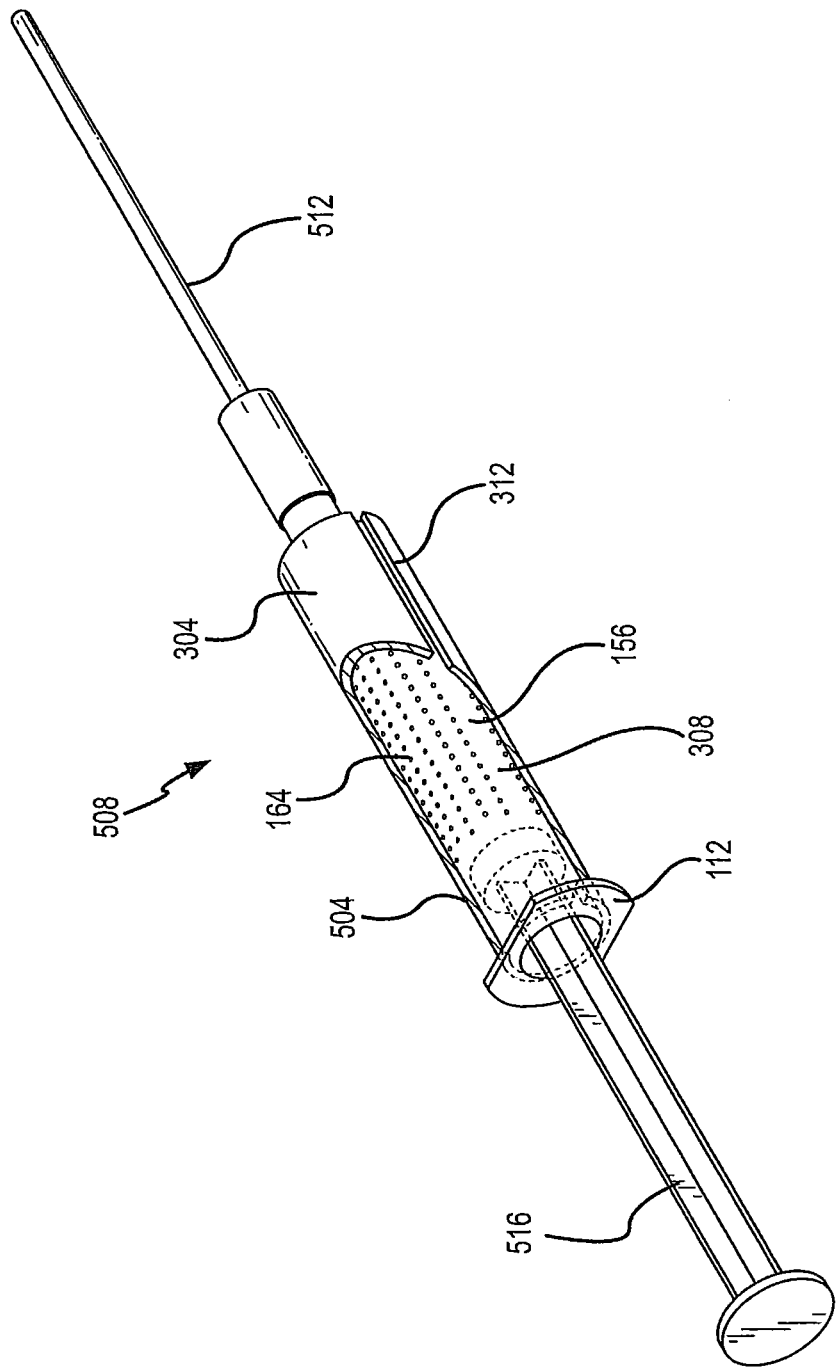

With reference now to FIG. 3B, an inner chamber 112 with an inner chamber sleeve 304 positioned over the body 156 of the inner chamber 112 is illustrated. Furthermore, the inner chamber sleeve 304 is shown partially cut away to illustrate that the perforations 164 have been covered by the inner chamber sleeve 304 such that the inner chamber 112 can comprise the body 504 of a syringe 508 consisting of the body 504, a reinjection cannula or needle 512 and a plunger 516. In addition, FIG. 3B illustrates the positioning of the slit 312 in the inner chamber sleeve 304 over the portion 308 of the inner chamber body 156 in which no perforations 164 are formed.

In accordance with other embodiments of the present invention, and with reference now to FIGS. 3C and 3D, the inner chamber sleeve 304 may itself be provided with a plurality of perforations 316. Furthermore, the perforations 316 may be arranged such that they register with corresponding perforations 164 in the inner chamber 112 (see FIG. 3C). Accordingly, the inner chamber sleeve 304 can be positioned such that the interior of the inner chamber 112 is in communication with the exterior of the inner chamber through the perforations 164 and 316, for example to collect tissue in the inner chamber 112 using a vacuum formed in the interior volume 108 (see FIG. 1) of the outer chamber 104. FIG. 3C therefore illustrates an inner chamber 112 and an inner chamber sleeve 304 configured for the collection of tissue in accordance with embodiments of the present invention. By rotating or otherwise moving the inner chamber sleeve 304 with respect to the inner chamber 112, such that the perforations 164 in the inner chamber are not registered with the perforations 316 in the inner chamber sleeve 304, the perforations 164 can all be sealed, for example to reinject tissue collected in the inner chamber 112 into a body (see FIG. 3D). The inner chamber 112 and the inner chamber sleeve 304 can then be associated with a reinjection cannula or needle 512 and a plunger 516, as shown in FIG. 3D, for reinjecting collected tissue.

Figure 4:
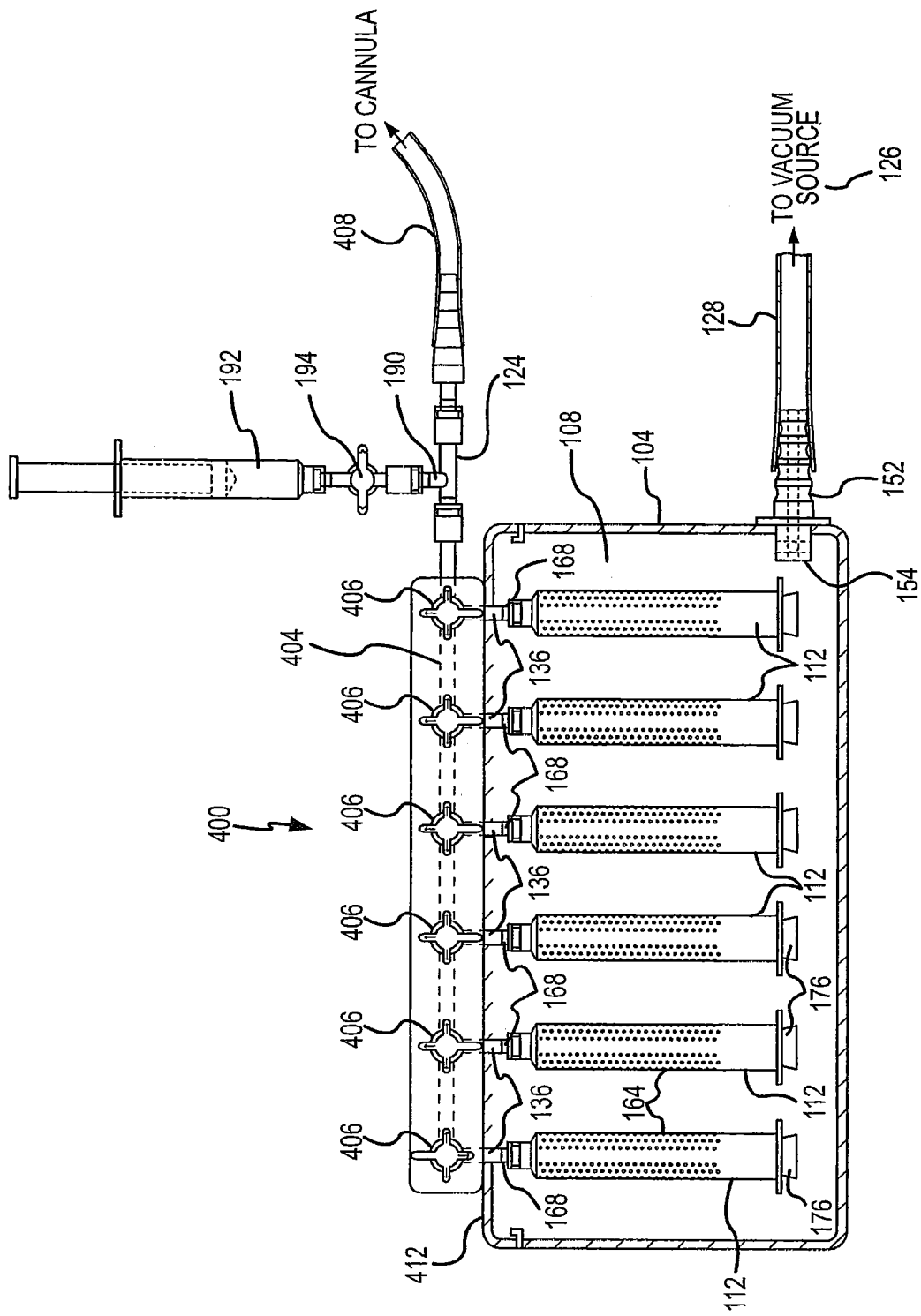
FIG. 4 is a cross-section of a device for tissue transplantation having multiple perforated inner chambers in accordance with embodiments of the present invention.

With reference now to FIG. 4, a tissue transplantation device 400 having multiple inner chambers 112 in accordance with embodiments of the present invention is depicted. As shown in FIG. 4, such embodiments may feature an outer chamber 104 having an interior volume 108 that is sufficiently large to house a number of inner syringes 112. According to such an embodiment, a manifold 404 is provided for delivering collected tissue to the inner chambers 112. An inlet 136 may be provided for each inner chamber 112, to interconnect the inner chambers 112 to the manifold 404. In accordance with embodiments of the present invention, the inlets 136 may comprise the female portion of a slip or lock type luer connector, such that the inlet 168 of an inner chamber 112 comprising the male portion of a corresponding luer connector can be securely received. In accordance with further embodiments of the present invention, the manifold 404 may be provided with stopcocks 406, to allow tissue to be collected in a selected inner chamber or chambers 112. In addition, by providing stopcocks 406, the device 400 can be used even if all of the inlets 136 associated with the manifold 404 are not connected to an inner syringe 112. Although the provision of stopcocks 406 in association with the manifold 404 can provide certain advantages, it should be appreciated that they are not required. In addition, a flexible tissue collection conduit 408 is provided for interconnecting the device 400 to a cannula.

In order to permit access to the inner volume 108, for example to insert an inner chamber 112, to remove one or more of the inner chambers 112 after the inner chambers 112 are full of collected tissue, or to clean the interior volume 108, the outer chamber 104 may be provided with an access panel or lid 412. As shown in FIG. 4, the access panel or lid 412 may incorporate or be attached to the manifold 404. Alternatively, a panel or lid 412 separate from the manifold 404 may be movable or removable to permit access to the interior volume 108 of the outer chamber 104.

As also illustrated in FIG. 4, the outer chamber 104 may generally be in the form of a box or other shape sized and arranged to contain a desired number of inner chambers 112. In addition, the outer chamber 104 of such an embodiment is substantially rigid so that a vacuum, for example a slight vacuum of about 8-12 inches of mercury, can be maintained within the interior volume 108 without collapsing the outer chamber 104. The outer chamber 104 may be formed from a transparent or translucent material, in whole or in part, to permit the amount of tissue collected in the inner chambers 112 to be viewed from outside of the outer chamber 104.

The outer chamber may additionally include a fitting or tube 152 having a tapered end, a nipple or other fitting to place the interior volume 108 in communication with a vacuum source 126 via a section of suction tubing 128. The tube 152 may optionally comprise or be associated with a filter 154 to collect fluids and other material drawn off of fat collected in the inner syringes.

In addition, embodiments of the present invention may provide an intermediate conduit 124 that provides an inlet 190 for fluid provided by fluid reservoir 192 in order to instill an additive or other fluid to tissue being drawn through the intermediate conduit 124 and/or to tissue that has been collected in the inner chambers 112. In accordance with embodiments of the present invention, the fluid reservoir 192 may comprise a syringe. A stopcock 194 may be provided between the fluid reservoir 112 and the fluid conduit 124.

With reference now to FIGS. 5A-5C, various embodiments of an inner syringe 112 configured for reinjecting collected tissue into a body are illustrated. In connection with each of the illustrated configurations, the inner syringe 112 is shown with an inner chamber sleeve 304 covering the perforations 164 in the inner syringe 112. Accordingly, the inner chamber 112 and inner chamber sleeve 304 combine to form the body 504 of a syringe 508. The syringe 508 also includes a reinjection cannula or needle 512 and a plunger 516 inserted into the interior bore 160 of the inner chamber 112. As shown in FIGS. 5A-5C, the reinjection cannula 512 may be interconnected to an inner chamber inlet 168 comprising the male portion of a luer connector by a body member 520 comprising the female portion of a luer connector.

With particular reference now to FIG. 5A, the inner chamber 112 is incorporated into a syringe 508 comprising a conventional manual syringe with a thumb operated plunger arm 524. The manual syringe may also comprise handles to provide a control syringe. In FIG. 5B, the inner chamber 112 is shown incorporated as part of a syringe 508 operated by a mechanical ratchet plunger 528. In FIG. 5C, the inner chamber 112 is shown as part of a syringe 504 interconnected to a compressed air type injection device or mechanical linear displacement device 536. In connection with a compressed air device, the operator can selectively allow compressed air to force the plunger 516 against tissue collected in the inner syringe 112, to reinject that tissue into a body.

As can be appreciated by one of skill in the art after consideration of the description provided herein, fat collected in an inner chamber 112 does not need to be removed from the inner chamber 112 until it is reinjected into a body. In order to configure the inner syringe 112 for reinjection of collected tissue, an inner chamber sleeve 304 is positioned such that the perforations 164 in the body 156 of the inner chamber 112 are blocked. In connection with embodiments incorporating in inner chamber sleeve 304 that slips over the outside of the inner chamber 112, blocking the perforations 164 may comprise inserting the body 156 of the inner chamber 112 into the sleeve 304. In accordance with embodiments utilizing an inner chamber sleeve 304 adapted for insertion within the interior bore 160 of the inner chamber 112, the inner chamber sleeve 112 is slipped into the interior volume 160, separating the collected tissue from the perforations 164 in the wall of the inner chamber body 156. In accordance with embodiments of the present invention utilizing an inner chamber sleeve 304 that includes perforations 316, configuring the inner chamber 112 for the reinjection of tissue may comprise rotating the inner sleeve 304 from a position in which the provided holes 316 register with the perforations 164, to a position such that the holes 316 are out of registration with the perforations 164, and the perforations 164 are therefore blocked.

In addition, the inlet 168 of the inner chamber 112 is interconnected to a reinjection cannula 512, the end plug 176 is removed from the proximal end 172 of the inner chamber 112, and a plunger 516 is inserted into the interior bore 160 of the inner chamber 112 through the open proximal end 172. The syringe 504 thus formed using the inner chamber 112 is then ready for manual reinjection of tissue, or for association with an injection device for use in connection with reinjection.

Figure 6:
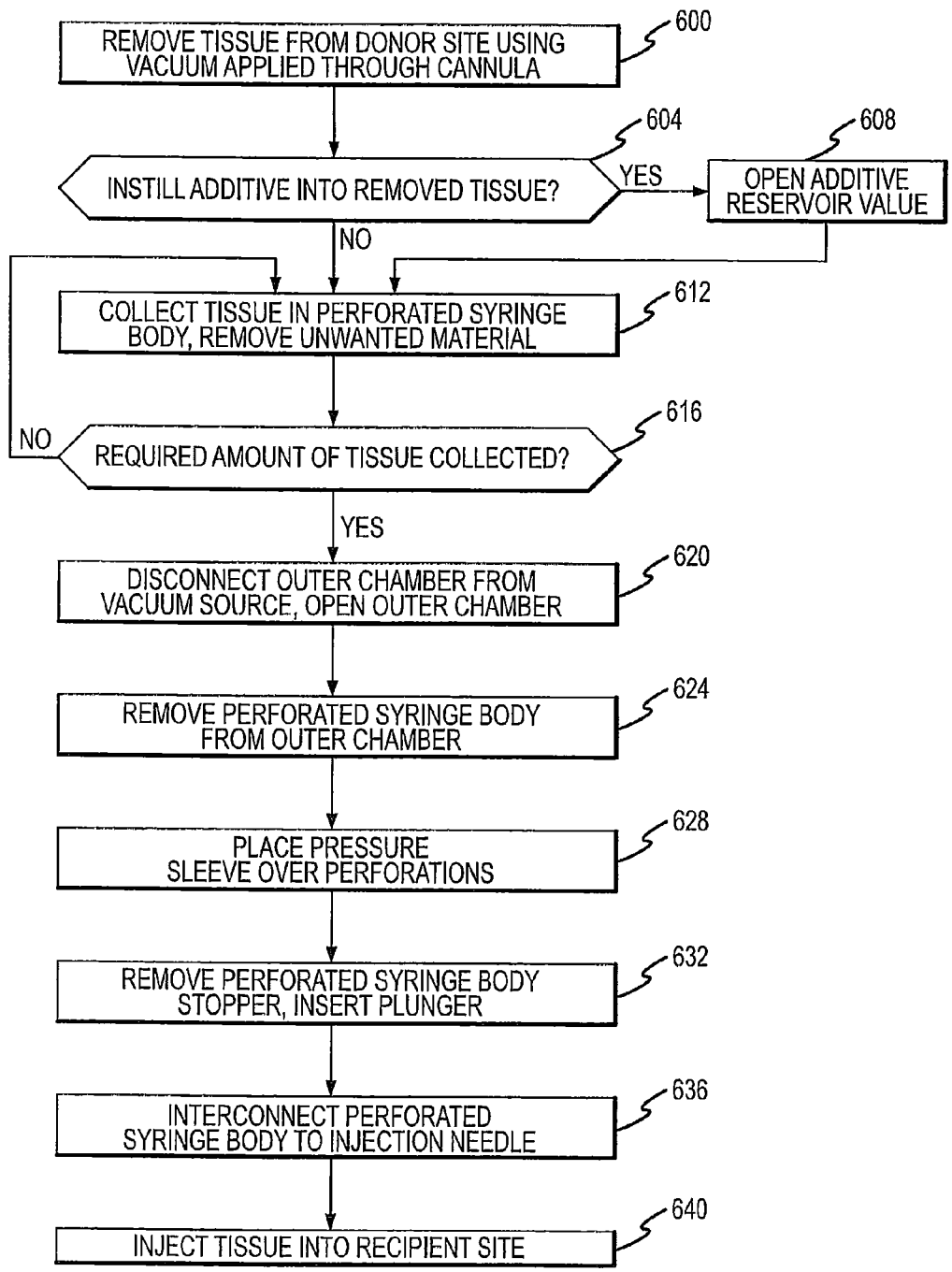
FIG. 6 is a flowchart depicting aspects of a method for transplanting tissue in accordance with embodiments of the present invention.

With reference now to FIG. 6, aspects of a method for transplanting tissue in accordance with embodiments of the present invention are illustrated. Initially, at step 600, tissue is removed from a donor site using a vacuum applied to that site through a cannula 116. In accordance with embodiments of the present invention, a vacuum of about 8 to 10 inches of mercury is applied using a vacuum source 126. At step 604, it can be determined whether an additive or other fluid is to be instilled into the removed tissue. If an additive or other fluid is to be instilled into the removed tissue, the fluid can be introduced to the flow of collected tissue. That is, the fluid can be instilled while the tissue flows through the intermediate conduit 124. In connection with adding the fluid, a stopcock or valve 194 controlling communication between a fluid reservoir 192 and the intermediate conduit 124 can be opened (step 608). In addition, a plunger provided as part of the fluid reservoir 192 can be manipulated to provide additional control to the amount of fluid introduced to the flow of tissue. Alternatively or in addition, an additive or other fluid can be instilled in collected tissue after collection.

The removed tissue is collected in the perforated inner chamber body 156, and unwanted materials removed from the collected fat through the provided perforations 164 (step 612). As can further be appreciated, the unwanted materials tend to be drawn from the interior bore 160 of the inner chamber 112 and towards the tube 152 and the vacuum conduit 128.

At step 616, a determination may be made as to whether the required amount of tissue has been collected (step 616). If the required amount of tissue has not been collected, the process may return to step 612.

Once the required amount of tissue has been collected, the outer chamber 104 can be disconnected from the vacuum source 126, and the outer chamber 104 can be opened (step 620). In connection with an embodiment of the present invention such as illustrated in FIG. 1, disconnecting the outer chamber 104 from the vacuum source 126 and opening the outer chamber 104 may comprise removing the plug 148 from the proximal end of the outer chamber body 132. In connection with a device 400 such as illustrated in FIG. 4, disconnecting the outer chamber 104 from the vacuum source 126 may comprise turning off the vacuum source 126 and opening the outer chamber 104 may comprise opening an access panel 412. After opening the outer chamber 104, the inner chamber 112 may be removed from the interior volume 108 of the outer chamber 104 (step 624).

After the inner chamber 112 is removed from the outer chamber, a pressure or inner chamber sleeve 304 may be positioned over the perforations 164 in the body 156 of the inner chamber 112 (step 628). Positioning an inner chamber sleeve 304 over the perforations 164 may comprise sliding the sleeve 304 over an exterior of the inner chamber 112, such that the perforations 164 are covered. Alternatively, placing a sleeve 304 over the perforations 164 may comprise sliding a pressure sleeve into the interior of the inner chamber 112. According to still other embodiments, placing the sleeve 304 over the perforations 164 may comprise rotating an inner chamber sleeve 304 having perforations 316 such that the perforations 316 of the sleeve 304 are out of registration with the perforations 164 in the inner chamber 112, blocking the perforations 164 in the inner chamber 112. Accordingly, placing an inner chamber sleeve 304 over the perforations 164 prevents communication between the interior bore of the inner chamber 112 and the exterior of the inner chamber through the perforations 164.

The stopper or plug 176 in the end of the inner chamber 112 may then be removed, and a plunger 516 (see e.g., FIGS. 5A-5D) may be inserted into the interior bore 160 of the inner chamber 112 (step 632). The inner chamber 112 thus can form the body of a syringe 508 and may be interconnected to a reinjection cannula 512 (step 636). The completed syringe 504 may then be used to reinject the removed tissue into a recipient site (step 640). Examples of techniques for reinjecting tissue include manual operation of the syringe 504, operation of a syringe using a mechanical ratchet type gun (e.g., as shown in FIG. 5B), and injection using a compressed air type injection device (e.g., as illustrated in FIG. 5C).

Figure 7:
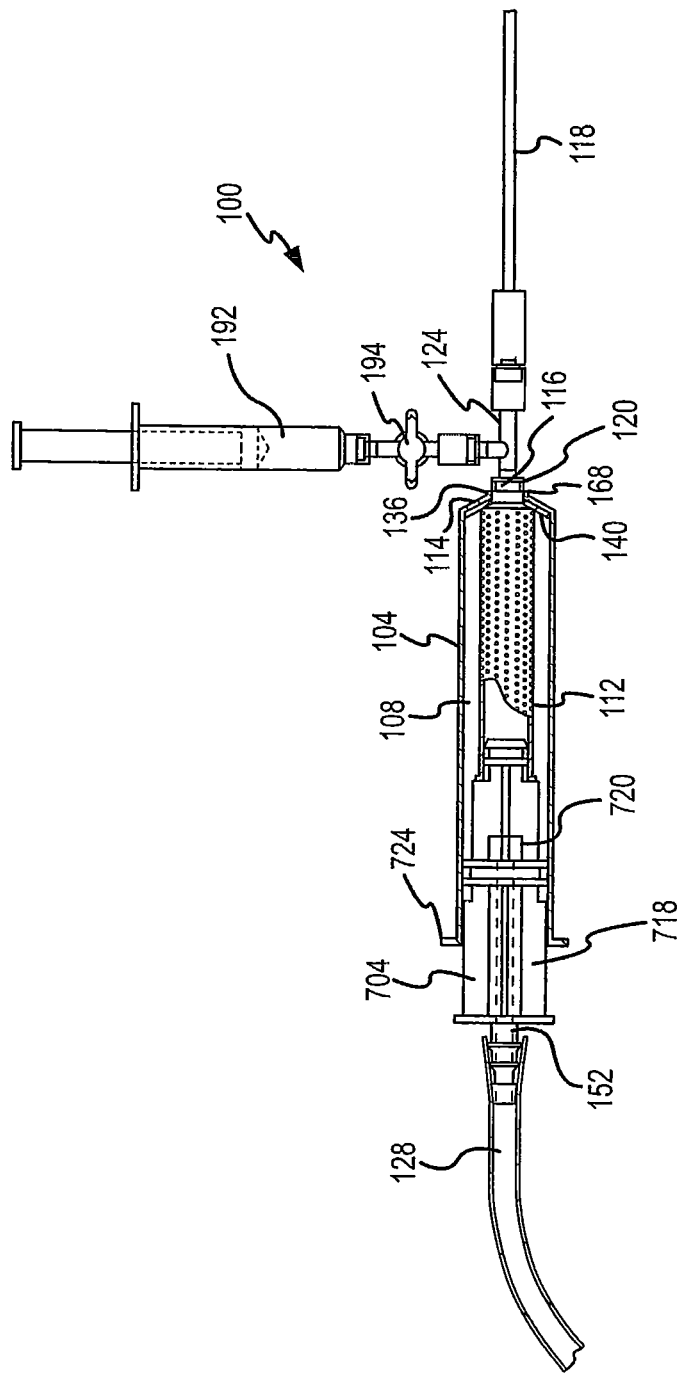
FIG. 7 is a cross-section of a device for tissue transplantation in accordance with other embodiments of the present invention.
Figure 8:
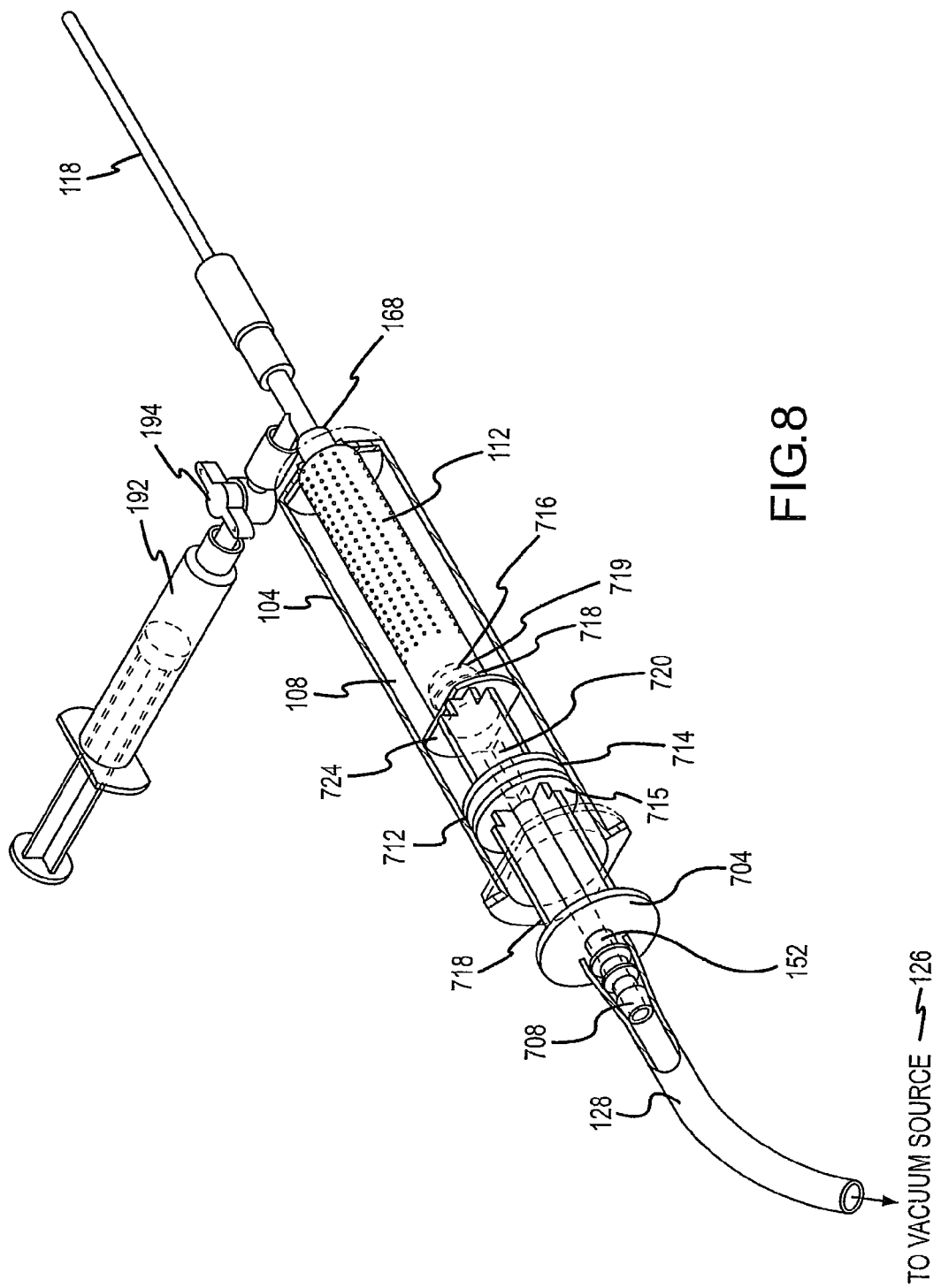
FIG. 8 is a partially cutaway perspective view of the device for tissue transplantation illustrated in FIG. 7.

In FIG. 7, a cross-section of a device 100 for tissue transplantation in accordance with other embodiments of the present invention is illustrated. In FIG. 8 the device 100 of FIG. 7 is shown in a partially cutaway perspective view. In general, the device 100 illustrated in FIGS. 7 and 8 includes an outer chamber 104 that defines an interior volume 108 sized to accommodate a perforated inner chamber 112. Accordingly, the device 100 illustrated in FIGS. 7 and 8 is, at least in certain respects, the same as or similar to the device 100 illustrated in FIG. 1. However, the device 100 illustrated in FIGS. 7 and 8 includes an integrated plug unit 704 in place of the separate plugs or stoppers 148 and 176 shown in FIG. 1. The integrated plug unit 704 generally includes an outer chamber seal 712 and in inner chamber seal 716. More particularly, the outer chamber seal 712 of the integrated plug unit 704 is received by the open proximal end 144 of the outer chamber 104, while the inner chamber seal 716 is received by the open proximal end 172 of the inner chamber 112. In accordance with embodiments of the present invention, the seals 712, 716 are each formed by an O-ring 714, 718 carried within a grooved disk 715, 719. In addition, the integrated plug unit 704 may include lateral walls 718 extending from the center axis of the integrated plug unit 704, to assist in maintaining the alignment of the integrated plug unit 704 with respect to the outer chamber 104.

The integrated plug unit 704 incorporates a tube 152 comprising a nipple, tapered stub or other fitting to which the suction tubing 128 can be interconnected. Furthermore, the tube 152 extends through the plug unit 704 from the proximal portion 708 interconnected to the suction tube 128 at least to an opening 720 between the outer chamber seal 712 and the inner chamber seal 716. Accordingly, through the opening 720, the interior volume 108 of the outer chamber 104 can be placed in communication with the vacuum source 126, allowing a vacuum to be created within the interior volume 108.

As shown in FIG. 8, the perforated inner chamber 112 of embodiments of the present invention may comprise a handle 724. Furthermore, the handle 724 can be sized such that portions of the handle 724 are in contact with the interior surface of the outer chamber 104, to assist in maintaining the alignment of the perforated inner chamber 112 with respect to the outer chamber 104. In particular, the handle 724 and the inlet 168 of the perforated inner chamber 112 may assist in maintaining the perforated inner chamber 112 and the outer chamber 104 in axial alignment.

The provision of an integrated plug unit 704 reduces the number of separate components that a user is required to handle in connection with using the tissue transplantation device 100, as compared to certain other embodiments. In addition, it can be appreciated that an integrated plug unit 704 can accommodate inner chambers 112 having different lengths by adjusting the distance that a plug unit 704 is inserted into the outer chamber 104.

Figure 9:
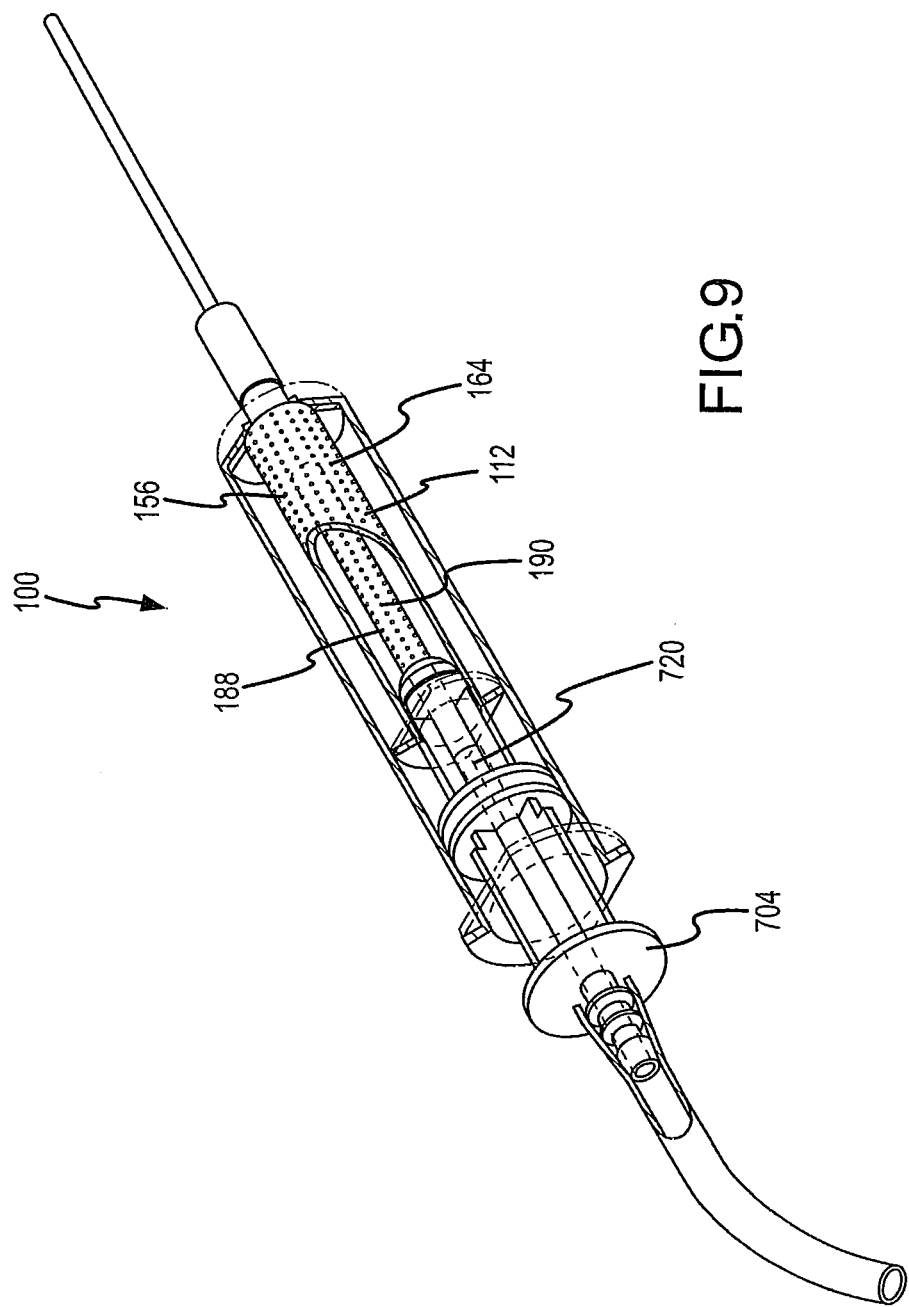
FIG. 9 is a partially cutaway perspective view of a device for tissue transplantation in accordance with other embodiments of the present invention.

With reference now to FIG. 9, a tissue transplantation device 100 in accordance with still other embodiments of the present invention is illustrated. In particular, the perforated inner chamber 112 is shown partially cut away to reveal a perforated central suction tube 188 extending from an integrated plug unit 704 into the interior of the inner chamber 112. The perforated central suction tube 188 may be interconnected to or integral with the integrated plug unit 704 of the embodiment in FIG. 9. Furthermore, the central suction tube 188 includes a closed distal end and an open proximal end that is in communication with the vacuum tube 128 through the tube 152. Accordingly, the central tube 152 in such embodiments extends through the inner chamber seal 716 such that a vacuum can be applied from the center portion of the perforated inner chamber 112, as well as from the outer diameter. In addition to the central suction tube 188, an opening 720 between the outer chamber seal 712 and the inner chamber seal 716 is provided to create a vacuum within the interior volume 108 of the outer chamber 104 around the exterior of the inner chamber body 156. In accordance with embodiments of the present invention, the perforated central suction tube 188 may include perforations 190 that are sized and arranged in the same or in a similar fashion as the perforations 164 in the body 156 of the inner chamber 112.

Figure 10:
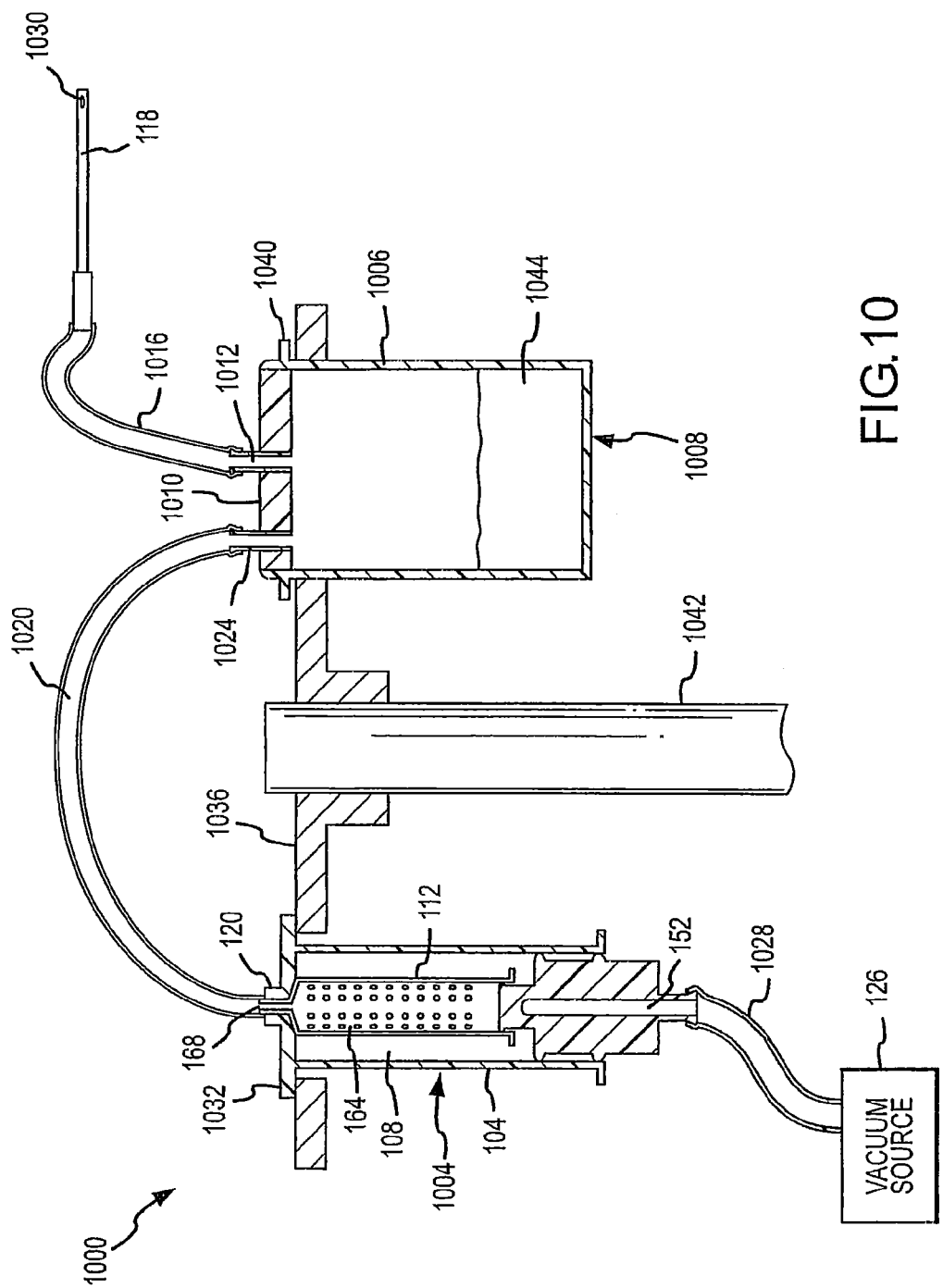
FIG. 10 is a cross-section of a device or system for tissue transplantation that includes a tissue-washing reservoir in accordance with embodiments of the present invention.

FIG. 10 depicts a device or system for tissue transplantation 1000 in accordance with other embodiments of the present invention, in cross-section. In general, the system 1000 is similar to other systems 100 in accordance with other embodiments of the present invention, in that it includes a tissue collection reservoir or filtering apparatus 1004 that includes an outer chamber 104 defining an interior volume 108 sized to accommodate an inner chamber or filter 112. In addition to the tissue collection reservoir 1004, the tissue transplantation system 1000 includes a tissue-washing reservoir 1008. The tissue-washing reservoir 1008 generally comprises a vessel 1006 with a lid 1010. The lid 1010 may incorporate an inlet 1012 and an outlet 1024. In accordance with embodiments of the present invention, the inlet 1012 is formed in about the center of the lid 1010, while the outlet 1024 is formed towards the edge of the lid 1010. In accordance with other embodiments of the present invention, the inlet 1012 and the outlet 1024 are formed in opposite halves of the lid 1010.

The tissue-washing reservoir 1008 generally receives tissue harvested from a body using a cannula 118 that is connected to the inlet 1012 of the tissue washing reservoir 1008 by a flexible intermediate conduit or cannula conduit 1016. The tissue transplantation system 1000 also includes a washed material or tissue conduit 1020 interconnecting the outlet 1024 of the tissue collection reservoir 1004 to the inlet 168 of the inner chamber 112 of the tissue collection reservoir 1004. In addition, the tissue transplantation system 1000 includes a vacuum source conduit 1028 interconnecting the outlet tube 152 of the tissue collection reservoir 1004 to the vacuum source 126. Accordingly, the vacuum source 126 can create a vacuum in the interior volume 108 of the tissue collection reservoir 1004. Moreover, because of the interconnection to the tissue-washing reservoir 1008 by the washed tissue conduit 1020, a vacuum may be created in the tissue washing reservoir 1008. The vacuum in the tissue-washing reservoir 1008 can in turn create a vacuum at the inlet 1030 to the cannula 118 via the cannula conduit 1016 that can be used to aspirate tissue from a body. Accordingly, the system for tissue transplantation permits the aspiration or removal of tissue from a body, washing and collection in a single, uninterrupted process or system. Moreover, injection of removed and washed tissue back into a body can be performed directly from the inner chamber 112 of the tissue collection reservoir 1004, for example as discussed in connection with other embodiments of the present invention. In accordance with embodiments of the present invention, the various inlets 120, 1012 and outlets 152, 1024 may comprise Luer connectors that mate with the various conduits 1016, 1020, 1028.

Considering the components included in the tissue transplantation system 1000 illustrated in FIG. 10 now in more detail, the tissue collection reservoir 1004 includes a mounting member 1032 that cooperates with a support 1036. Similarly, the tissue-washing reservoir 1008 includes a mounting member 1040 that cooperates with the support 1036. The support 1036 may in turn be interconnected to or held by a stand 1042, such as a Mayo stand. In accordance with other embodiments of the present invention, the tissue collection reservoir 1004 may be directly interconnected to a stand 1042. In the illustrated embodiment, the inlets 120, 1012 of the tissue collection reservoir 1004 and the tissue washing reservoir 1008 are at the top of their respective reservoir 1004, 1008. In the case of the tissue collection reservoir 1004, the placement of the inlet 120 at the top of the tissue collection reservoir 1004 can facilitate the collection of tissue within the inner chamber 112, while helping to avoid clogging of the perforations or holes 164 in the inner chamber 112 before the inner chamber 112 is substantially filled with tissue. In the case of the tissue washing reservoir 1008, the positioning of the inlet 1012 at the top of the reservoir 1008 facilitates the deposition of tissue removed using the cannula 118 in the reservoir 1008 In addition, the tissue-washing reservoir 1008 is held such that the outlet 1024 is also at the top of the tissue washing reservoir 1008. This configuration prevents the removal of tissue and any washing solution or other liquid 1044 for washing or treating removed tissue before washing or treatment is completed. In addition, the mounting members 1032 and/or 1040 can be configured to facilitate the removal of the associated reservoir 1004 or 1008 from the support 1036 by a practitioner.

Figure 11:
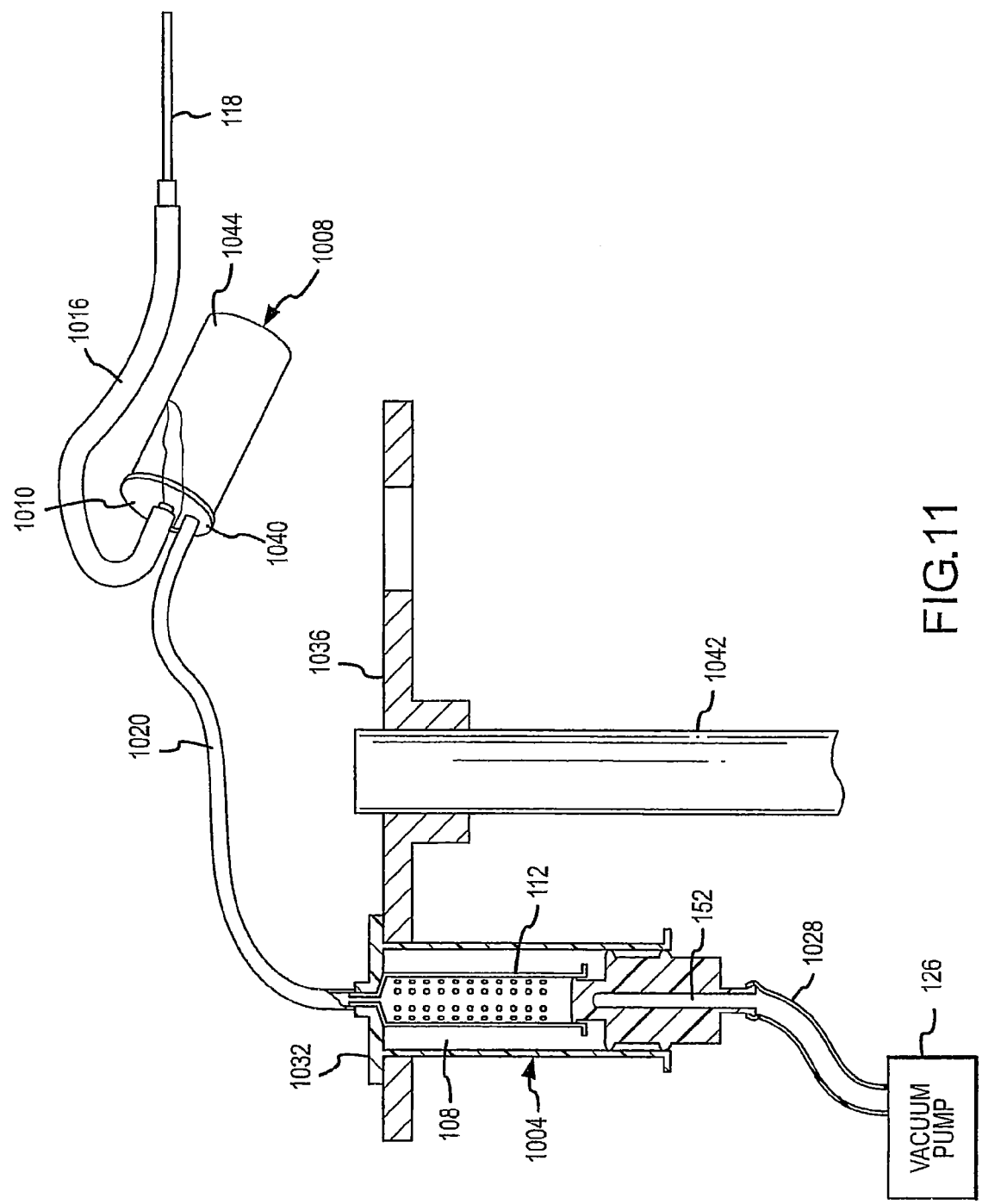
FIG. 11 is a cross-section of another embodiment of the device or system for tissue transplantation, including a tissue-washing reservoir in accordance with embodiments of the present invention.

As can be appreciated by one of skill in the art from the description provided herein, when the tissue washing reservoir 1008 is held in an upright position, such that the inlet 1012 and the outlet 1024 are at the top of the tissue washing reservoir 1008, tissue removed from a body using a cannula 118 is deposited through the inlet 1012 into any liquid 1044 held by the tissue washing reservoir 1008. In order to remove collected tissue from the tissue washing reservoir 1008, the tissue washing reservoir 1008 is removed from the support 1036 and tipped, such that the tissue and any liquid 1044 covers the outlet 1024, allowing the tissue and liquid 1044 to be suctioned out of the tissue washing reservoir 1008. This configuration of the system 1000 is illustrated in FIG. 11.

In accordance with embodiments of the present invention, the mounting members 1032 and/or 1040 can comprise simple flanges that support the associated reservoir 1004, 1008 with a hole formed in the support member 1036 for receiving a reservoir 1004 or 1008. Accordingly, removal of a reservoir 1004 or 1008 can comprise lifting the reservoir 1004, 1008 out of the hole in the support member 1036. In accordance with other embodiments of the present invention, different mounting member 1032, 1040, support member 1036, and/or stand 1042 configurations can be provided. For example, the mounting member 1032, 1040 can comprise a plate with holes for interconnecting to the mating support structure 1036, for example provided as part of or connected to a stand 1042. In accordance with other embodiments of the present invention, the mounting members 1032, 1040 may incorporate a loop of cable or rope for hanging the associated reservoir 1004 or 1008 from a conventional stand 1042 incorporating a support structure 1036. Accordingly, a mounting member 1032 or 1040, support structure 1036 and stand 1042 are not limited to any particular configuration, and instead can be any structure suitable for holding a reservoir 1004, 1008 in a desired orientation. In general, mounting members 1032, 1040 and support structure 1036 preferably facilitate the detachment of the tissue collection reservoir 1004 in order to remove the inner chamber 112 and configure it for the insertion of tissue, and facilitate the removal of the tissue washing reservoir 1008 in order to tip the reservoir in connection with transferring washed tissue to the tissue collection reservoir 1004 in a simple and straightforward manner.

Figure 12:
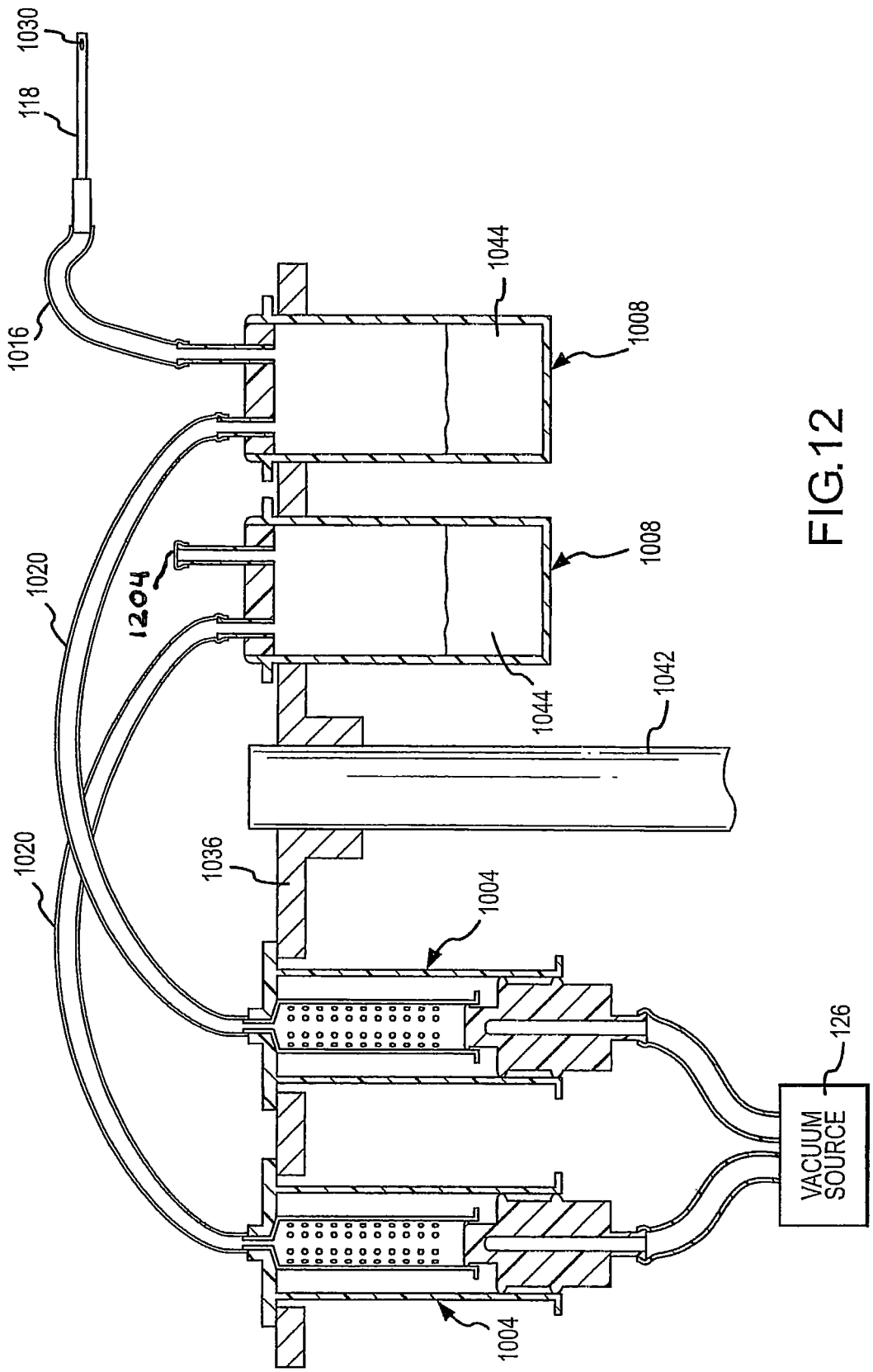
FIG. 12 depicts the device or system for tissue transplantation of FIG. 11, with the washing reservoir removed from the mount for transfer of washed tissue.

FIG. 12 illustrates another embodiment of a system 1000 in accordance with embodiments of the present invention. In accordance with such an embodiment, multiple tissue collection reservoirs 1004 and/or multiple tissue washing reservoirs 1008 may be provided and interconnected to a common support member 1036, or a plurality of support members 1036. By providing multiple reservoirs 1004 and/or 1008, the opportunity to process and collect more tissue than with a single tissue washing reservoir 1008 and tissue collection reservoir 1004 can be provided. In accordance with embodiments having multiple parallel circuits of collection reservoirs 1004 and washing reservoirs 1008, a cap 1204 may be provided to ensure adequate vacuum at the inlet 1030 of the cannula 118. In addition, different arrangements and interconnections of reservoirs 1004, 1008 can be provided. For example, a plurality of tissue washing reservoirs 1008 can be connected in series, for example to provide multiple saline baths or treatment in different solutions.

Figure 13:
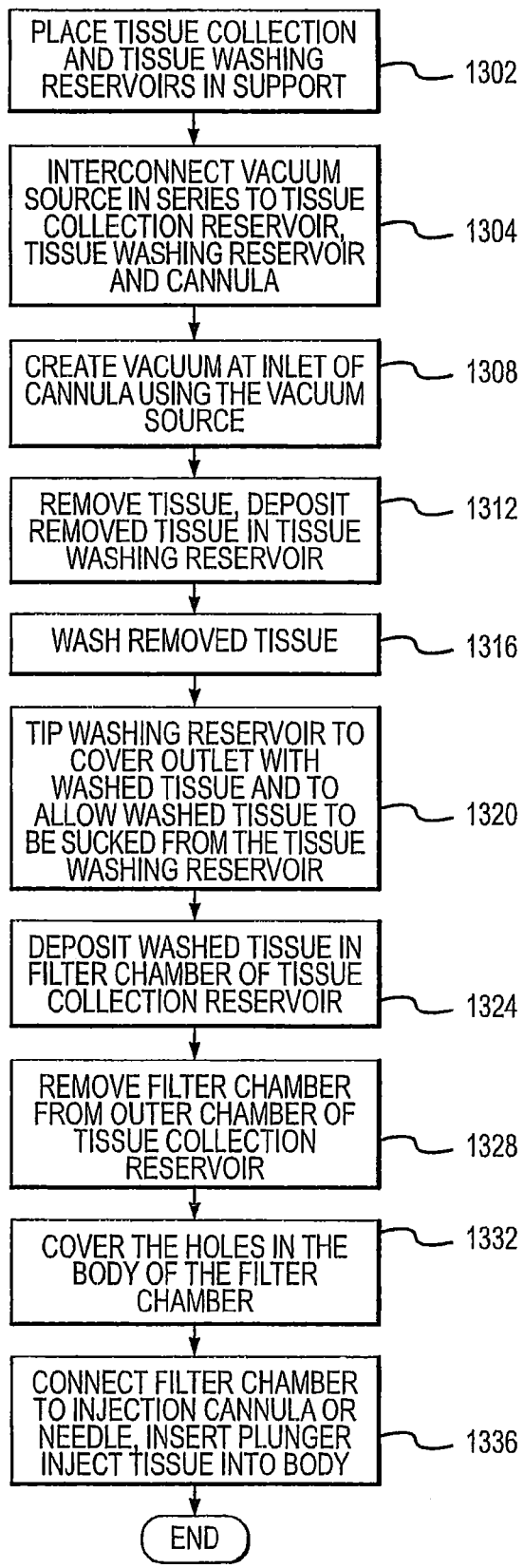
FIG. 13 is a flowchart depicting aspects of a method for washing transplanting tissue in accordance with embodiments of the present invention.

FIG. 13 illustrates aspects of a method for removing tissue from a body and washing the tissue to prepare it for reinjection. Moreover, the method does not require that a practitioner handle tissue directly. Initially, at step 1302, the tissue collection reservoir 1004 and the tissue-washing reservoir 1008 may be placed in a support 1036, such that the inlets 120, 1012 to the respective reservoirs are at or near the top of the reservoirs 1004, 1008. In addition, a liquid irrigant 1044 may be placed in the vessel 1006 of the tissue-washing reservoir 1008. At step 1304, the vacuum source 126 is interconnected in series to the tissue collection reservoir 1004, the tissue washing reservoir 1008 and the cannula 118. In accordance with embodiments of the present invention, interconnecting the vacuum source with these components may comprise interconnecting the inlet of the vacuum source 126 to the outlet 152 of the tissue collection reservoir 1004 outer chamber 104 using a vacuum source conduit 1028. Interconnecting the vacuum source 126 to other components may further include interconnecting the inlet 120 to the inner chamber 112 of the tissue collection reservoir 1004 to the outlet 1024 of the tissue-washing reservoir 1008 using a washed material or tissue conduit 1020. The interconnection of components to the vacuum source 126 may be completed by interconnecting the inlet 1012 of the washed tissue reservoir 1008 to the cannula 118 using a flexible intermediate conduit or cannula conduit 1016.

At step 1308, a vacuum is created at the inlet 1030 to the cannula 118 by activating the vacuum source 126. Accordingly, it can be appreciated that a vacuum is created within the inner volume 108 of the tissue collection reservoir 1004, and within the tissue-washing reservoir 1008. Moreover, it can be appreciated that while the tissue-washing reservoir 1008 is at or near the top of the tissue washing reservoir 1008, liquid irrigant 1044, washed tissue, or other material in the tissue washing reservoir 1008 will not be removed from that reservoir 1008 by the vacuum.

The practitioner then removes tissue from the body, by inserting the cannula 118 in an area of desired tissue, allowing the tissue to be aspirated. The removed tissue is deposited in the tissue-washing reservoir 1008 (step 1312). The removed tissue may then be washed (step 1316). Washing of the removed tissue may comprise allowing the removed tissue to collect in the tissue washing reservoir 1008 while the tissue washing reservoir 1008 is at least partially filled with a liquid irrigant 1044. Alternatively or in addition, washing the removed tissue may comprise adding a liquid irrigant 1044 to tissue that has been collected in the tissue-washing reservoir 1008.

After washing the removed tissue, the tissue-washing reservoir 1008 is tipped so that the washed tissue and/or liquid irrigant 1044 contained in the tissue washing reservoir 1008 covers the outlet 1024, allowing the washed tissue and liquid irrigant to be sucked from the tissue-washing reservoir 1008 (step 1320). The washed tissue that has been sucked from the tissue-washing reservoir 1008 is conveyed by the washed material or tissue conduit 1020 to the interior of the inner chamber 112 of the tissue collection reservoir 1004 and deposited in the inner chamber 112 (step 1324). As described in connection with other embodiments of the present invention, the inner chamber 112 functions as a filter that collects removed tissue, while allowing other material to be separated from the removed tissue through perforations or holes 164 in the body of the inner chamber 112. In accordance with embodiments of the present invention, deposition of the washed tissue in the inner or filter chamber 112 is performed while the inlet to the inner chamber 112 is at or near the top of the inner chamber 112. In this orientation, washed tissue tends to collect first at the bottom of the inner chamber 112, and then fills towards the inlet 120. Accordingly, gravity can assist in keeping the inlet 120 to the inner chamber 112 clear, such that entry to the inner chamber 112 by additional washed tissue before the inner chamber 112 is full or substantially full of washed tissue is not prevented or impeded.

Following the collection of washed tissue in the inner or filter chamber 112, the inner or filter chamber 112 can be removed from the tissue collection reservoir 1004, with the washed tissue contained within the inner chamber 112 (step 1328). The holes or perforations 164 in the body of the filter chamber 112 can then be covered, for example using a sleeve 304, as described in connection with other embodiments of the present invention (step 1332). The filter chamber 112 can then be connected to an injection cannula or needle 512, a plunger 524 can be inserted into the filter chamber 112, and the washed tissue can be injected from the inner chamber 112 into the body (step 1336). As described in connection with other embodiments of the present invention, the plunger 524, injection needle 512, and sleeve 504 are added to the inner chamber 112 after the inner chamber 112 has been removed from the tissue collection reservoir 1004, to form an injection syringe.

As can be appreciated by one of skill in the art after consideration of the present disclosure, embodiments of the present invention allow for the removal, washing, and reinjection of tissue without requiring that a practitioner manually handle the tissue. Moreover, embodiments of the present invention provide a sealed system, allowing a single vacuum source 126 to provide suction for use in connection with removing tissue, moving tissue from the washing reservoir 1008 to the tissue collection reservoir 1004, and removing material from washed tissue while the washed tissue is held in a filter chamber 112. In addition to removing the need to manually handle and transfer tissue, embodiments of the present invention provide an integrated system with the included components either connected to one another or in convenient proximity to one another.

In accordance with embodiments of the present invention, the amount of liquid irrigant 1044 comprising a bath for washing removed tissue may be selected by the practitioner. In accordance with embodiments of the present invention, liquid irrigant 1044 may be supplied in a proportion of one part liquid irrigant 1044 to four parts removed tissue. In accordance with other embodiments of the present invention, liquid irrigant may be supplied in a proportion of one part liquid irrigant 1044 to eight parts removed tissue. In accordance with still other embodiments of the present invention, the proportion of liquid irrigant 1044 to removed tissue can be 5 to 1. As can be appreciated by one of skill in the art, by providing a reservoir, a practitioner can select the proportion of liquid irrigant 1044 to washed tissue that the practitioner deems appropriate. Examples of liquid irrigant volumes that can be useful in connection with procedures involving the removal, washing and reinjection of tissue range from 1 cc to about 500 cc's, with 150 cc's being a useful amount for many procedures.

Although certain embodiments of the present invention have been discussed in connection with a tissue washing reservoir 1008 that can be lifted or otherwise removed from a support member 1036 to tip the washing reservoir 1008 and thereby cover the outlet 1024 to remove washed tissue, other configurations are possible. For example, the tissue washing reservoir 1008 may be integral to a support member 1036, which is in turn removable from the stand 1042 to allow tipping of the tissue washing reservoir 1008. In accordance with still other embodiments of the present invention, the tissue-washing reservoir 1008 may be hinged or otherwise connected to a stand 1042 in such a way as to allow the outlet 1024 to be selectively covered for removal of washed tissue.

In accordance with embodiments of the present invention, materials that can be used in connection with constructing or forming the tissue collection reservoir 1004 vessel 1006 include polymers, glass or stainless steel. The vessel 1006 may also comprise a semi-rigid IV bag or any other container capable of maintaining a volume for liquid irrigant 1044 and/or removed tissue while a vacuum is formed in the vessel 1006. The preferred volume for the tissue collection reservoir vessel 1006 is about 80 cc's, although useful ranges include vessels having a volume from about ⅓ cc to 1500 cc's.

Figure 14:
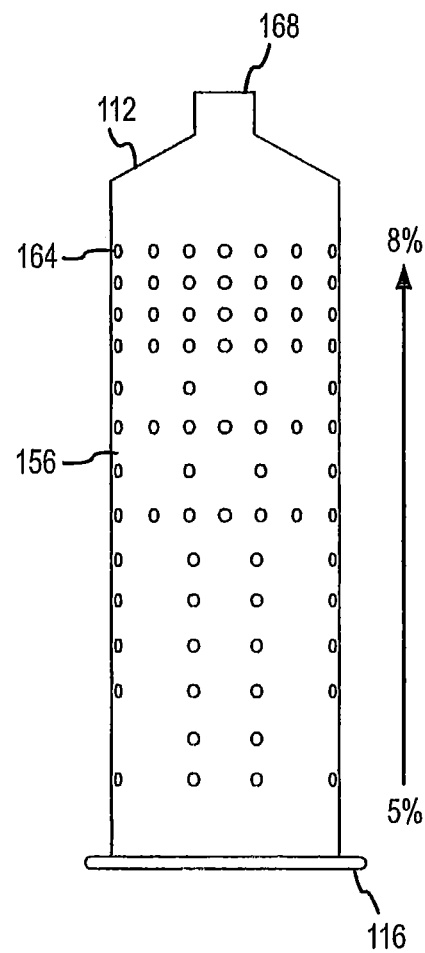
FIG. 14 is a side elevation of an inner chamber in accordance with other embodiments of the present invention.

FIG. 14 depicts an inner chamber for filter 112 in accordance with other embodiments of the present invention. In particular, the inner chamber 112 shown in FIG. 14 features holes or slits that vary in distribution over the length of the inner chamber 112. More particularly, the percentage of the surface area of the body 156 of the inner chamber 112 is greater towards the inlet 168 than towards the distal end 116 of the inner chamber 112. For example, the percentage of the area of the inner chamber body portion 156 comprising perforations or slits 164 may be about 25% towards the inlet 168 of the inner chamber 112, while the percentage of the area of the body portion 156 comprising perforations or slots 164 towards the distal end 116 of the inner chamber 112 may be about 3%. In accordance with other embodiments of the present invention, the whole percentage may range from 5% towards the distal end 116 of the inner chamber 112, and gradually increase to 8% towards the inlet 168. A configuration such as illustrated in FIG. 14 of perforations or slits 164 that provide a greater whole percentage towards the inlet 168 than towards the distal end 116 can prevent premature clogging of the inner chamber 112. For example, where the inner chamber 112 is oriented as shown in FIG. 14, with the inlet 168 generally above the distal end 116, gravity pulls most of the collected fat down towards the distal end 116. At the same time, the vacuum created by the vacuum source or pump 126 that pulls the fat and its accompanying liquid waste into the inner chamber 112 through the inlet 168 also pulls some of the small particles of cell walls through the holes 164, which can result in blocking or plugging of the perforations 164. Moreover, when a relatively large number of holes 164 become plugged, the entire inner chamber 112 can become plugged prematurely, preventing or inhibiting the continued collection of tissue. By providing a greater percentage of holes towards the inlet 168 of the inner chamber 112, the time of harvest or collection can be extended as compared to an inner chamber 112 with perforations 164 that are evenly distributed across the body portion 156.

In accordance with embodiments of the present invention, a device 100 for transplanting tissue may comprise an outer syringe 104 in the form of a substantially rigid cylindrical tube or syringe body formed from a clear polymer, such as polypropylene acrylic or polycarbonate. Other example materials from which the outer chamber 104 can be formed include metal, ceramic, other polymers and glass. Although transparent materials are desirable because they allow the inner chamber 112 to be viewed, for example to determine when the inner chamber 112 is full, they are not required. In accordance with exemplary embodiments of the present invention, the capacity of the interior volume 108 of the outer container 104 may be from about 10 cc to about 100 cc. In accordance with still other embodiments of the present invention, the interior volume 108 or capacity of the outer chamber 104 is about 60 cc. The outer chamber 104 may additionally feature an inner diameter of from about 0.5 inches to about 2 inches. In accordance with further embodiments, the inner diameter of the outer chamber 104 is about 1 inch. The thickness of the outer syringe may, in accordance with embodiments of the present invention, range from about 0.0156 inches to about 0.250 inches, and is about 0.0625 inches in an exemplary embodiment. The proximal open end 144 may have an inside diameter of from about 0.5 inch to 1.5 inch. In accordance with further embodiments, the open end 144 may have an inside diameter of about 1 inch. The plug 148 may have a central hole that is from about 0.065 inch to about 0.25 inch in diameter, which may extend for the entire length of the plug 148. In accordance with further embodiments, the plug 148 may have a central hole that is about 0.125 inch in diameter. The distal 114 or inlet 136 end of the outer chamber 104 may include a center hole that is from about 0.21 to about 0.5 inches in diameter. In accordance with embodiments of the present invention, the center hole at the inlet 136 of the outer chamber 104 is about 0.37 inch. Furthermore, the inlet 136 is configured to allow the inlet 168 of the inner chamber 112 to exit the interior volume 108 of the outer chamber 104.

In accordance with embodiments of the present invention in which a plurality of inner chambers 112 can be simultaneously contained within the interior volume 108 of the outer chamber 104, such as illustrated in FIG. 4, the outer chamber 104 may be generally in the form of a box. Examples of materials from which the outer chamber 104 of such embodiments can be formed include clear or translucent acrylic or clear or translucent polymer. Other materials suitable for forming the outer chamber or box 104 in embodiments containing multiple inner chambers 112 include glass, translucent polymers, opaque polymers, and other clear polymers. Although not necessary, a transparent material is desirable in order to allow the amount of tissue that has been collected in the inner chambers 112 to be viewed. In accordance with an exemplary embodiment, the box is from about 2 to 10 inches high, 6 to 12 inches long, and 4 to 12 inches deep. In a further exemplary embodiment, the box is about 8 inches high, about 8 inches long, and about 6 inches deep. In addition, the outer chamber 104 is air tight and includes a resealable lid or access panel 412. The wall thickness of the outer chamber 104 may range from about 0.1 inch to about 0.25 inch, and in accordance with an exemplary embodiment of the present invention wall thickness is about 0.125 inch. Furthermore, the material and thickness should be selected so that the outer chamber 104 does not collapse as a result of the creation of a vacuum within the inner volume 108. In accordance with still other embodiments, the outer chamber 104 may be configured to hold any number of inner chambers 112. For example, the outer chamber 104 can be configured to contain 6 inner chambers 112. Furthermore, individual stopcocks 406 can be provided in the manifold 404, for example where operation with less than a maximum number of inner chambers 112 is desired.

According to embodiments of the present invention, the inner chamber 112 is formed from clear or translucent polycarbonate polymers or acrylic. Other suitable materials include other glass. As an example, the interior volume of the inner syringe 112 may be from about 0.25 cc to about 60 cc. In accordance with embodiments of the present invention, the interior volume of the inner chamber 112 is about 10 cc. The inlet 168 may comprise a slip or lock type luer connector having an internal diameter from about 0.05 inches to about 0.25 inches. In accordance with embodiments of the present invention, the internal diameter of the luer connector may be about 0.07 inches.

The perforations 164 may each have a diameter from about 0.015 inches to about 0.03 inches. In accordance with certain embodiments, the perforations 164 may have a diameter of about 0.02 inches. The perforations 164 may be arranged such that there are from about 75 to 150 holes per square inch. In accordance with other embodiments, the holes or perforations 164 may be arranged such that there are 86.8 holes per square inch. Furthermore, the total number of perforations 164 may range from about 300 to about 1000 perforations 164 in an inner chamber 112 having a capacity of about 10 cc. In accordance with further embodiments, an inner chamber 112 having a capacity of about 10 cc may have about 350 perforations 164. Furthermore, the filter area provided by the inner chamber 112 may be from about 4 to about 5 inches for a 10 cc capacity inner chamber 112. As a particular example, the filter area of an inner chamber 112 having a 10 cc volume may be about 4.3 square inches.

The length of the inner chamber 112 may range from about 2 inches to about 10 inches. In a particular example, the inner syringe has a length of about 4 inches. The diameter of the inner chamber 112 may be from about 0.1 inches to 1.5 inches. In a particular example, the diameter of the inner chamber 112 is about 0.5 inches. As noted above, the capacity of the inner chamber 112 may be about 10 cc. In accordance with other embodiments, the capacity of the inner chamber 112 may range from about 0.25 cc to about 60 cc.

If provided, an inner chamber 112 inner suction tube 188 may be formed from polymer, glass, metal or ceramic material, and the bore in the end plug 176 places in the interior of the interior of the inner suction tube 188 in communication with the interior volume 108 of the outer chamber 104. In accordance with embodiments of the present invention, the inner tube 188 may have a length that is about 90 percent of the length of the inner syringe, plus or minus 5 percent. In accordance with other embodiments, the inner collection tube 188 may extend into the interior volume of the inner chamber 112 for a distance equal to about 0 percent to about 90 percent of the length of the inner chamber body 156. The diameter of the suction line 128 may range from about 0.075 to about 0.55 inches. In an exemplary embodiment, the diameter of the inner tube is about 0.125 inches. The diameter of the holes or perforations in the tube 188 may range from about 0.015 to about 0.03 inches. In a particular embodiment, the collection tube 188 contains 30 holes having a diameter of about 0.02 inches.

The cover sleeve 304 may be formed from an acrylic, polymer or polycarbonate or other translucent or clear material. In connection with a cover sleeve 304 that includes perforations 308 and is generally left in place about the exterior of the inner chamber 112 while collecting tissue, the sleeve 304 will generally be formed from a transparent material, to permit viewing of the interior of the inner chamber 112. Furthermore, the interior diameter of the cover sleeve 304 may be slightly smaller than the external diameter of the inner chamber 112, to provide a tight fit and may be split. In accordance with still other embodiments, the sleeve 304 may be adapted for insertion inside the inner chamber 112, in which case it should be formed from a thin material, for example a stiff walled tube having a wall thickness of about 0.04 inch. If holes or perforations 316 are provided, they may be about the same size as the holes or perforations 164 in its inner chamber 112.

In accordance with embodiments of the present invention, a tissue transplantation device 100 may be a disposable device that is not intended for reuse. In accordance with other embodiments of the present invention, a tissue transplantation device 100 may be capable of resterilization, to enable reuse. In accordance with still other embodiments of the present invention, components of a tissue transplantation device 100 may be reusable, while other components of that tissue transplantation device 100 may be disposable.

Although the foregoing contains particular ranges with respect to exemplary embodiments of the present invention, those dimensions are not intended to be limiting. Instead, they are examples of dimensions that have been found to be, or that are believed to be, useful in connection with particular implementations of embodiments of the present invention.

Figure 15:
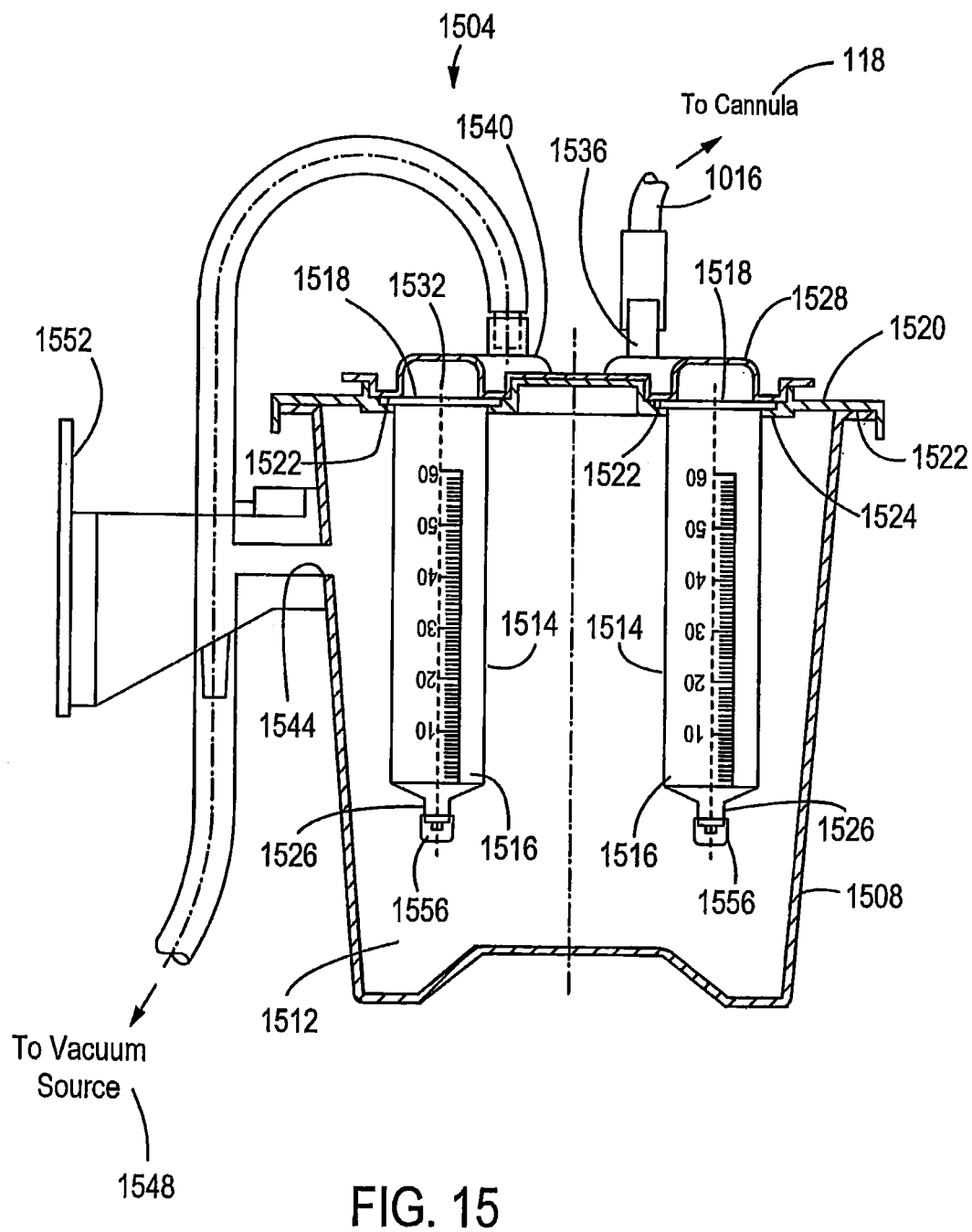
FIG. 15 is a cross section of a device for collecting tissue in accordance with embodiments of the present invention.

FIG. 15 illustrates a device for collecting tissue 1504 in accordance with further embodiments of the present invention. In general, the device for collecting tissue 1504 includes a canister 1508 defining, at least in part, an interior volume 1512 comprising a vacuum chamber. Located within the vacuum chamber 1512 is a collection vessel 1514. In the embodiment illustrated, the collection vessel 1514 comprises a plurality of syringe bodies 1516. Although the embodiment illustrated in FIG. 15 includes a plurality of syringe bodies 1516, other embodiments may include a single syringe body 1516. The syringe bodies 1516 may comprise commonly available devices with an open end 1518 surrounded by a flat flange or handle 1522, and a tip 1526 opposite the open end 1518, that may comprise a luer-type connection capable of receiving a cannula or of being connected to tubing.

A syringe plate 1520 is interconnected to the canister 1508 at the top lip or edge 1522 of the canister 1508. The syringe plate 1520 features a hole or syringe mount 1524 for receiving a syringe body 1516. More particularly, the syringe plate 1520 includes a syringe mount 1524 for each syringe body 1516 that can be accommodated by the device for collecting tissue 1504. A syringe or transfer plate lid 1528 interconnects to the syringe or transfer plate 1520 to form a vacuum tight seal over the open tops 1518 of the syringe bodies 1516. In addition, the transfer plate 1520 and transfer plate lid 1528 cooperate with one another to form a tissue transfer channel 1532 that is in communication with the open tops 1518 of the syringe bodies 1516. An inlet 1536, which serves as an inlet for tissue to be delivered to the collection vessel 1514 or syringe bodies 1516, is formed at a first end or the tissue transfer channel 1532. A first vacuum outlet 1540, in communication with the interiors of the syringe bodies 1516, is formed at a second end of the tissue transfer channel 1532. A second vacuum outlet 1544, in communication with the interior 1512 of the canister 1508 is also provided. Both the first 1540 and second 1544 vacuum outlets may be connected to a common vacuum source 1548. A bracket 1552 may also be provided to facilitate mounting the device for collecting tissue 1504 to a support structure, such as a stand. In general, the inlet 1536 is interconnected to a cannula 118 by a length of tubing 1016. Accordingly, the device for collecting tissue 1504 can be used to receive tissue removed from a body through the cannula 118 and that is delivered by the tubing 1016 to the transfer channel 1532. The removed tissue then drops into the syringe bodies 1516 in sequence until all of the syringe bodies 1516 are filled. Caps 1556 on the ends of the syringe bodies 1516 prevent collected tissue from flowing out of the tips 1526 of the syringe bodies 1516.

Figure 16:
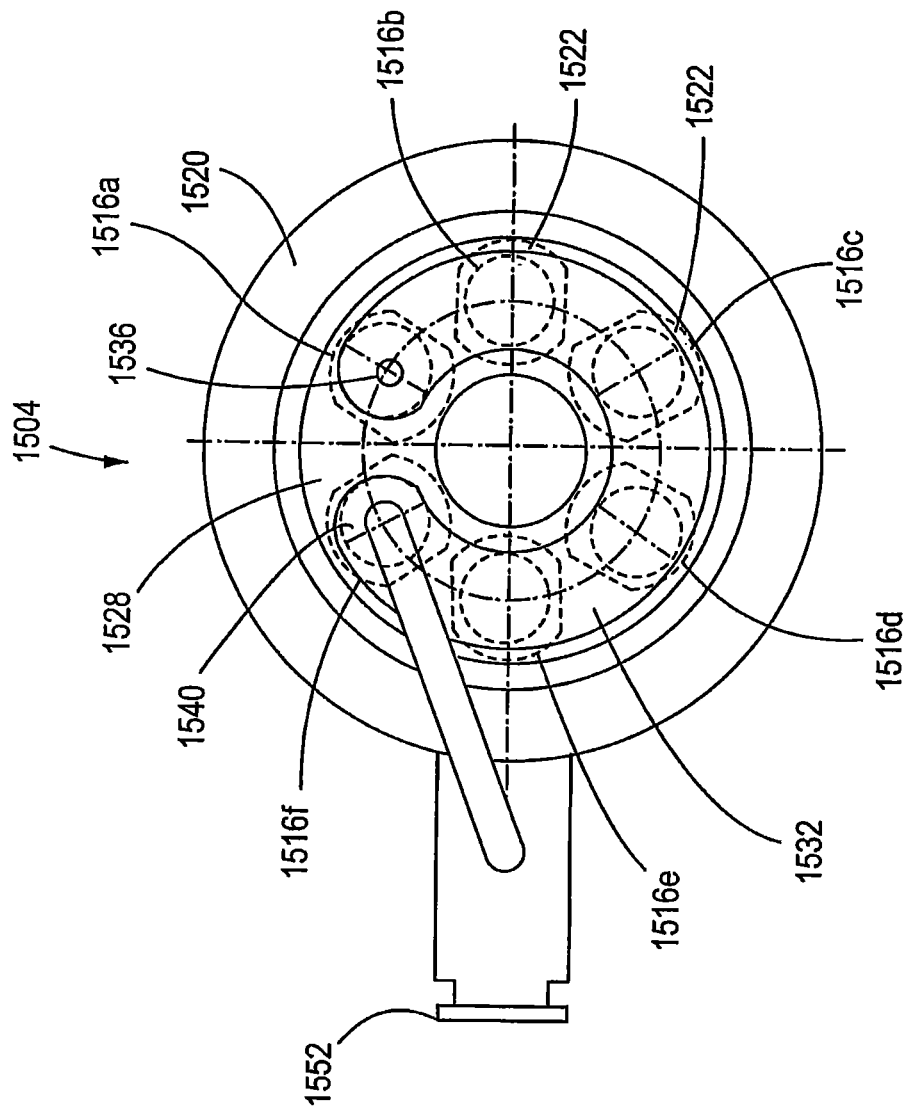
FIG. 16 is a plan view of a device for collecting tissue in accordance with embodiments of the present invention.

FIG. 16 illustrates the device for collecting tissue 1504 of FIG. 15 in plan view. As shown, the syringe bodies 1516 can be arranged in a circular pattern. Accordingly, the tissue transfer channel 1532 describes almost a complete circle. As tissue is received through the inlet 1536, it is deposited in the first syringe body 1516a. Once the first syringe body 1516a is filled with tissue, additional tissue received at the inlet 1536 is delivered by the tissue transfer channel 1532 to the second syringe body 1516b. This process can continue along the tissue transfer channel 1532 until the last syringe body 1516f is filled. Accordingly, the device for collecting tissue 1504 allows a practitioner to fill a plurality of syringe bodies 1516 with collected tissue, without requiring that the practitioner manually handle the tissue. In addition, the device for collecting tissue 1504 operates to automatically fill the plurality of syringe bodies 1516. Accordingly, a plurality of syringe bodies 1516 can be filled with collected tissue in a way that is convenient for the practitioner, and in a way that reduces the opportunity for collected tissue to become contaminated or damaged.

Figure 17:
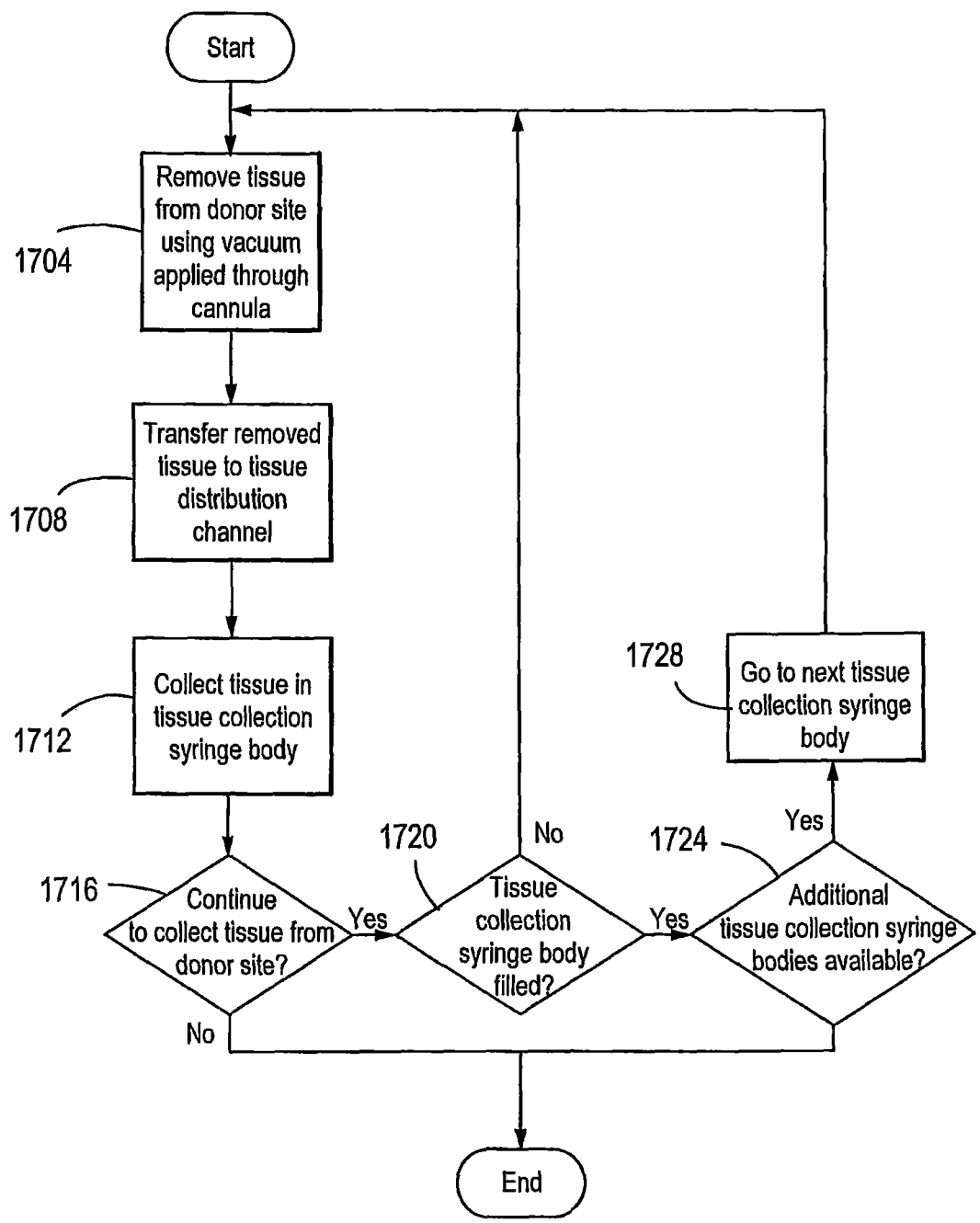
FIG. 17 is a flowchart illustrating aspects of the operation and use of a device for collecting tissue in accordance with embodiments of the present invention.

FIG. 17 is a flow chart illustrating aspects of the operation of a device for collecting tissue 1504 in accordance with embodiments of the present invention. Initially, tissue is removed from a donor site in a body using a vacuum from a vacuum source 1548, applied through a cannula 118 (step 1704). The removed tissue is transferred to a tissue transfer or distribution channel 1532, for example by a length of tubing 1016 interconnecting the cannula 118 to the inlet 1536 of the collection vessel 1516 (step 1708). The tissue is then collected in a syringe body 1516 (step 1712).

At step 1716, a determination and/or decision is made as to whether to continue to collect tissue from the donor site. If tissue is no longer to be collected, the process may end. If tissue remains to be collected from the donor site, for example more tissue is needed for an implantation procedure, a determination may then be made as to whether the tissue collection syringe body 1516 that had been receiving collected tissue has filled (step 1720). If that tissue collection syringe body 1516 has not filled, the process may return to step 1704, and the deposition of collected tissue into that syringe body 1516 can continue. If the tissue collection syringe body 1516 has filled with tissue, a determination is made as to whether an additional tissue collection syringe body 1516 is available (step 1724). If an additional tissue collection syringe body 1516 is not available the process may end. If an additional tissue collection syringe body 1516 is available, the process proceeds to step 1728, with the selection of the next tissue collection syringe 1516. The process may then return to step 1704, and removed tissue can be collected in the next tissue collection syringe body 1516. Accordingly, the tissue collection syringe bodies 1516 are filled in sequence. For example, with reference to FIG. 16, the syringe bodies will be filled in a sequence beginning with the first syringe body 1516a, proceeding to the second syringe body 1516b, then to the third syringe body 1516c, and so on through the fourth 1615d and fifth 1516e syringe bodies until the sixth syringe body 1516f is filled. Although certain examples of a device for collecting tissue 1504 in accordance with embodiments of the present invention have included six syringe bodies 1516, it should be appreciated that other numbers of syringe bodies 1516 can be used.

Figure 18:
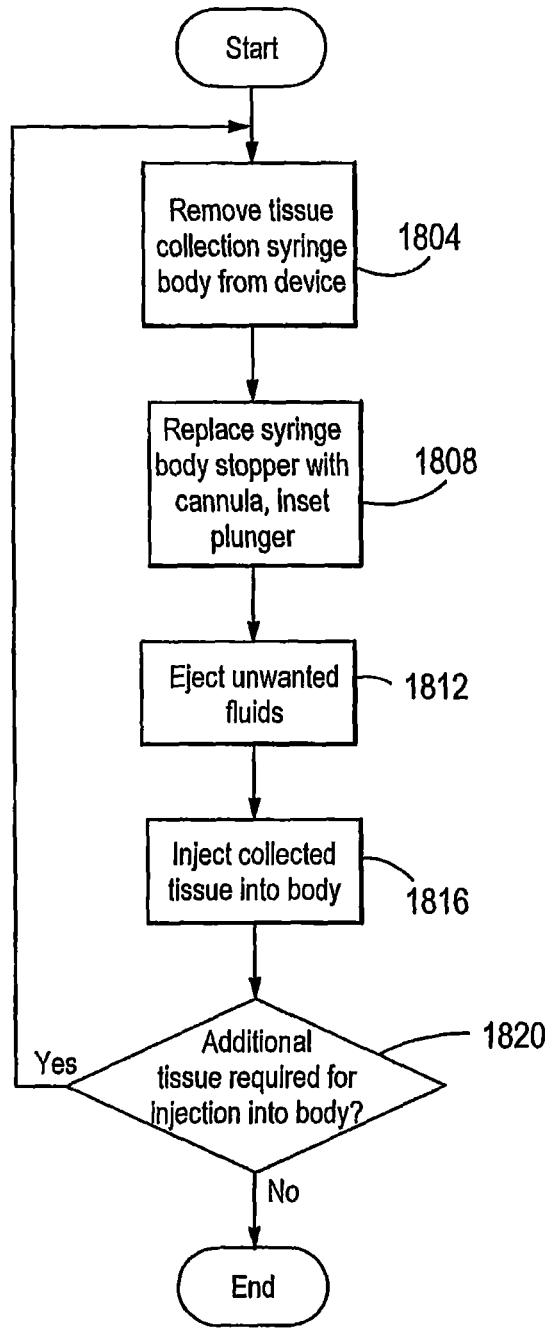
FIG. 18 is a flowchart illustrating other aspects of the operation and use of a device for collecting tissue in accordance with embodiments of the present invention.

With reference now to FIG. 18, additional aspects of the operation of a device for collecting tissue 1504 in accordance with embodiments of the present invention are illustrated. More particularly, the use of a device for collecting tissue 1504 in connection with injecting collected tissue into a body are illustrated. Initially, a tissue collection syringe body 1516 that is at least partially filled with collected tissue is removed from the device 1504 (step 1804). Removing a syringe body 1516 can include removing the tissue transfer plate lid 1528 from the transfer plate 1520, in order to access the syringe bodies 1516. In particular, a practitioner, by removing the transfer plate lid 1528 can lift any of the syringe bodies 1516 from the transfer plate 1520, and remove a syringe body 1516 from the syringe mount 1524 that held the syringe body 1516. After removing a syringe body 1516, the syringe body stopper 1556 can be replaced with a cannula 118, and a plunger 524 can be inserted into the syringe body 1516 (step 1808). At step 1812, unwanted fluids, such as additives or anesthetics, can be ejected from the syringe body 1516. For example, because fat that has been collected in a syringe body 1516 will tend to float above additives and other fluids, a practitioner can eject unwanted fluids by operating the plunger 1524 to force fluids at the bottom of the syringe body 1516 out of the syringe body 1516 (i.e. towards and through the tip 1526 and the cannula 118 (if fitted) while the syringe body 1516 is pointing downwardly). The syringe body stopper 1556 and cannula 118 may be provided with luer lock connectors and thus can be selectively interconnected to a cooperating luer lock connector at the distal end of the syringe body 1516. The collected tissue can then be injected into a receiving site in a body (step 1816). If desired, prior to injecting the collected tissue into a body, that tissue can be treated, for example by instilling additives or washing, while the collected tissue is in the syringe body 1516.

At step 1820, a determination can be made as to whether additional tissue is required for injection into a body, as part of the injection process. If additional tissue is required, the process may return to step 1804, and the practitioner can remove a second syringe body 1516 from the device 1504. If additional tissue is not required for injection, the process may end. As can be appreciated by one of skill in the art from the description provided herein, embodiments of the present invention provide a convenient way for a plurality of syringe bodies 1516 to be filled with collected tissue. Moreover, this can be accomplished without requiring that the practitioner manually transfer tissue from a larger collection chamber into individual syringes. Instead, the loading of multiple syringe bodies 1516 is accomplished automatically and without manual handling, using a closed system that is resistant to contamination and that avoids contacting harvested tissue with ambient air. In addition, the placement of collected tissue into syringe bodies 1516 of a size that is convenient for handling by the practitioner is facilitated.

The transfer plate 1520 and transfer plate lid 1528 are generally formed from an FDA approved resin, because these components 1520, 1528 can provide the transfer channel 1532 that guides collected tissue to syringe bodies 1516. In accordance with exemplary embodiments of the present invention, the tissue transfer channel 1532 may have a width of between ½ an inch to 2 inches, a height of between ½ an inch and 2 inches, and may be from 4-16 inches in length. In accordance with other embodiments of the present invention, the transfer channel may have a width of 1 inch, a height of 1 inch, and a length of 8 inches. In addition, the shape of the transfer channel 1532 can be linear, circular, or any other shape along which syringe bodies 1516 can be conveniently placed. However, the tissue transfer channel 1532 should have a first end, at which tissue is introduced, and a second end, opposite the first end, at which a vacuum outlet is formed, so that collected tissue can be introduced to syringe bodies located along the length of the tissue transfer channel 1532 in sequence. In operation, the components of the device for collecting tissue 1504 may be drawn together by the vacuum that is applied. Moreover, because of the use of a vacuum, at least the tissue transfer plate 1520 and tissue transfer lid 1528 must be sufficiently strong to maintain the desired dimensions of the tissue transfer channel 1532. Because the interior of the container 1508 is connected to the vacuum source, it should also be capable of maintaining its volume while a vacuum is introduced to the interior of the canister 1508.

Figure 19A:
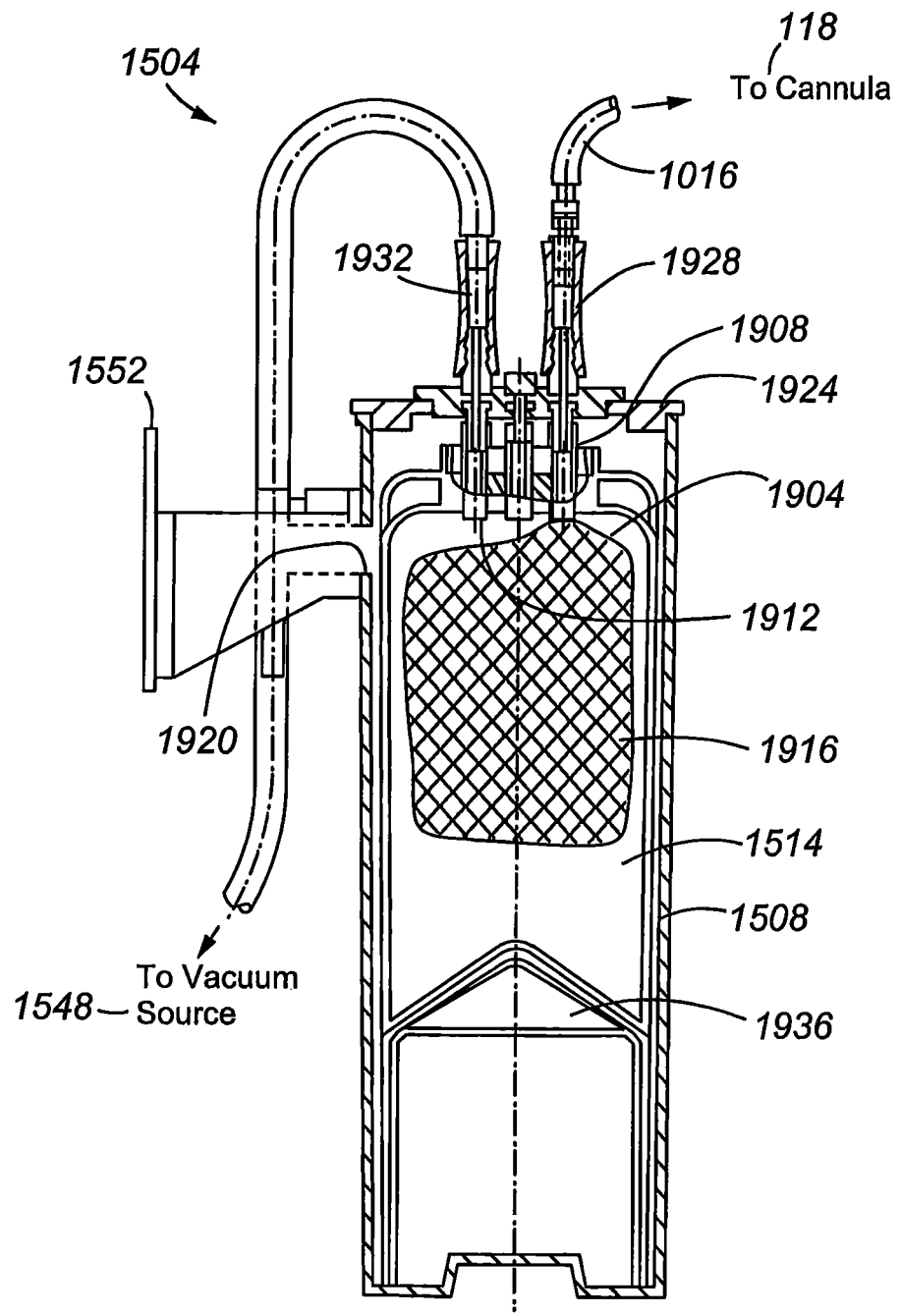
FIGS. 19A-19B are cross sections of devices for collecting tissue in accordance with other embodiments of the present invention.
Figure 19B:
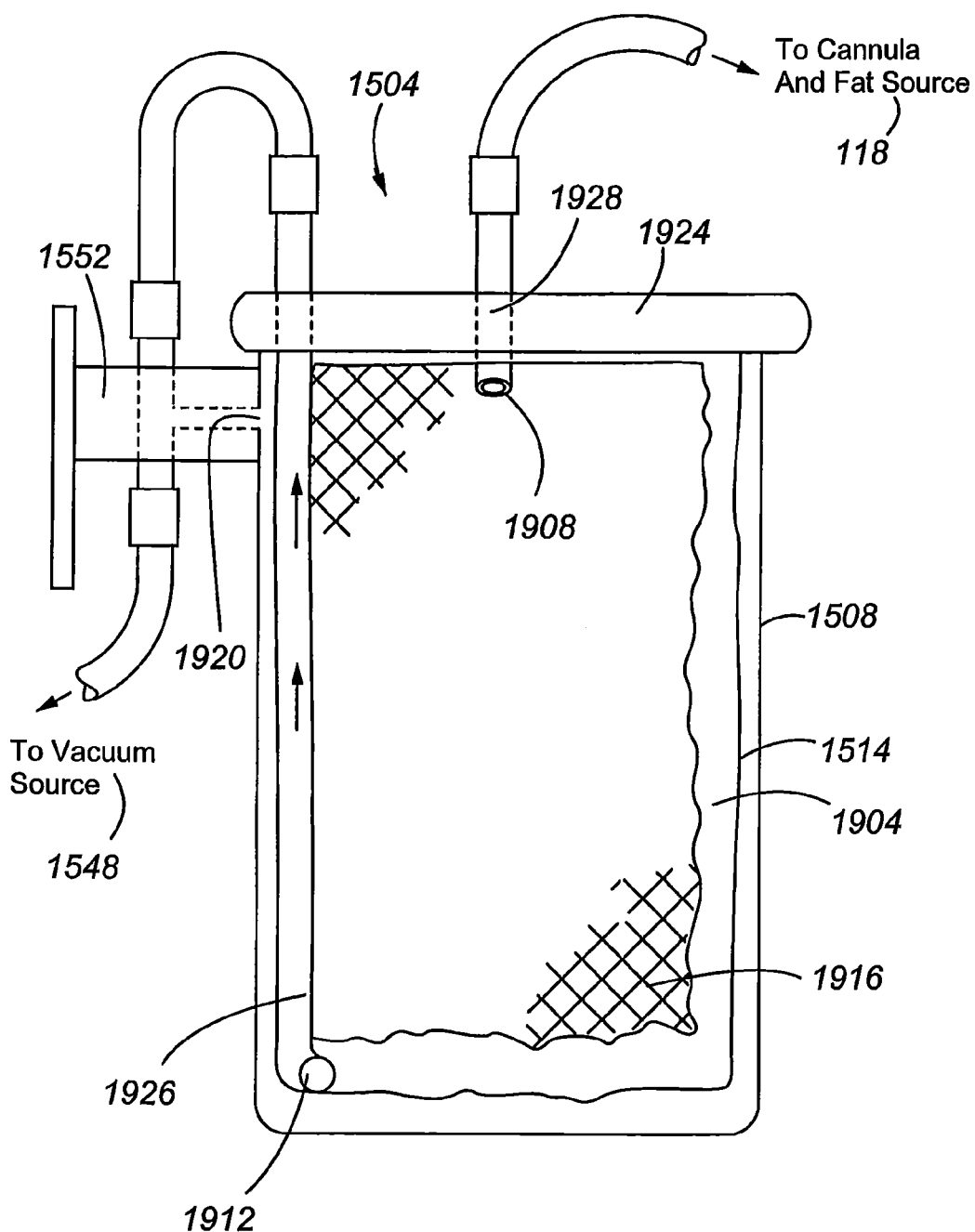

FIGS. 19A and 19B illustrate devices for collecting tissue 1504 in accordance with other embodiments of the present invention. In particular, devices for collecting tissue 1504 that includes a collection vessel 1514 comprising an impermeable outer tissue collection bag 1904 are illustrated in cross-section. The outer bag 1904 includes an inlet 1908, through which tissue collected using a cannula 118 can be admitted into the interior of the collection bag 1904. In addition, a first vacuum outlet 1912 is provided in communication with the interior of the collection bag 1904. The first vacuum outlet 1912 is also in communication with a vacuum source 1548. Accordingly, the vacuum from the vacuum source 1548 can be provided via the first vacuum outlet 1912 at the inlet to a cannula 118 for removing tissue from a body. In addition, the device for collecting tissue 1504 may include an inner tissue collection bag or filter 1916 that can be used to separate fat introduced into the interior of the outer collection bag 1904 via the intake 1908 from liquids or individual fat cells. In particular, the filter 1916 may be positioned within the outer collection bag 1904 so that fat is collected within the filter bag while liquids or small particles pass through the filter 1916 to the bottom of the outer collection bag 1904. The outer collection bag 1904 and filter 1916 (if provided) are held within a canister 1508. The canister 1508 may include a second vacuum outlet 1920 that is connected to the vacuum source 1548. By creating a vacuum within the interior of the canister 1508, the walls of the outer collection bag 1904 tend to be held apart from one another, promoting the deposition of tissue inside of the collection bag 1904. That is, the vacuum created within the canister 1508 and around the outside of the collection bag 1904 counter-acts the tendency of the collection bag 1904 to collapse due to the vacuum at the vacuum outlet 1912 in communication with the interior of the collection bag 1904.

The canister 1908 may be sealed at one end by a lid or seal assembly 1924. The seal assembly 1924 can include an inlet pathway 1928, providing communication between the tubing 1016 connected to the cannula 118, and the inlet 1908 to the inner bag 1916 and the outer collection bag 1904. The seal assembly 1924 can also provide a vacuum outlet pathway 1932 providing communication between the vacuum hose connected to the vacuum source 1548 and the first vacuum outlet 1912 in communication with the interior of the collection bag 1904. In addition, the canister 1508 may provide a support structure 1936 (see FIG. 19A), to support the bottom of the collection bag 1904. The canister 1508 may additionally include a bracket 1552 to facilitate interconnecting the device for collecting tissue 1504 to a support. As shown in the figures, a vacuum pathway tee 1940 may be formed in the bracket 1552 that connects the first 1912 and second 1920 vacuum outlets to the vacuum source 1548. Also, as shown, the second vacuum outlet may be formed in the bracket 1552, or may alternatively be separately formed in the wall of the canister 1508 and connected to the vacuum source 1548.

In the embodiment illustrated in FIG. 19B, the first vacuum outlet 1912 is formed at the end of a waste tube 1926 that extends from the seal assembly or lid 1924 generally at the top of the canister 1508 to the bottom of the outer collection bag 1904. Accordingly, the first vacuum outlet 1912 is located outside of the filter bag 1916 and at or towards the bottom of the outer collection bag 1904. In this location, the first vacuum outlet 1912 can pull liquid and other material that has passed through the filter bag 1916 and collected in the bottom of the outer collection bag 1904 out of the outer collection bag 1904. In this way, waste or otherwise unwanted materials can be separated from fat collected within the filter bag 1916, without requiring manual handling of the tissue collection bags 1904 and 1916.

In accordance with still other embodiments of the present invention, the waste tube 1926 can be formed at or along a seam of the outer tissue collection bag 1904. Accordingly, the waste tube 1926 can be integral to the outer tissue collection bag 1904. Moreover, in accordance with other embodiments of the present invention, the waste tube 1926 can also be integral or interconnected to the filter bag 1916. As with other embodiments of the present invention, by providing a second vacuum outlet 1920 in communication with an interior of the canister 1508, the tendency of the walls of the outer tissue collection bag 1904 to collapse the volume of the tissue collection bag 1904 is counteracted, to promote the deposition of tissue and other materials collected by a cannula 118 in the tissue collection bags 1904 and 1916 through the inlet 1908 to those bags 1904 and 1916. Thus, in accordance with embodiments of the present invention, the outer tissue collection bag 1904 is held open, with the opposing walls of the bag 1904 apart from one another, to form or increase the size of a tissue collection volume within the outer collection tissue bag 1904.

Figure 20:
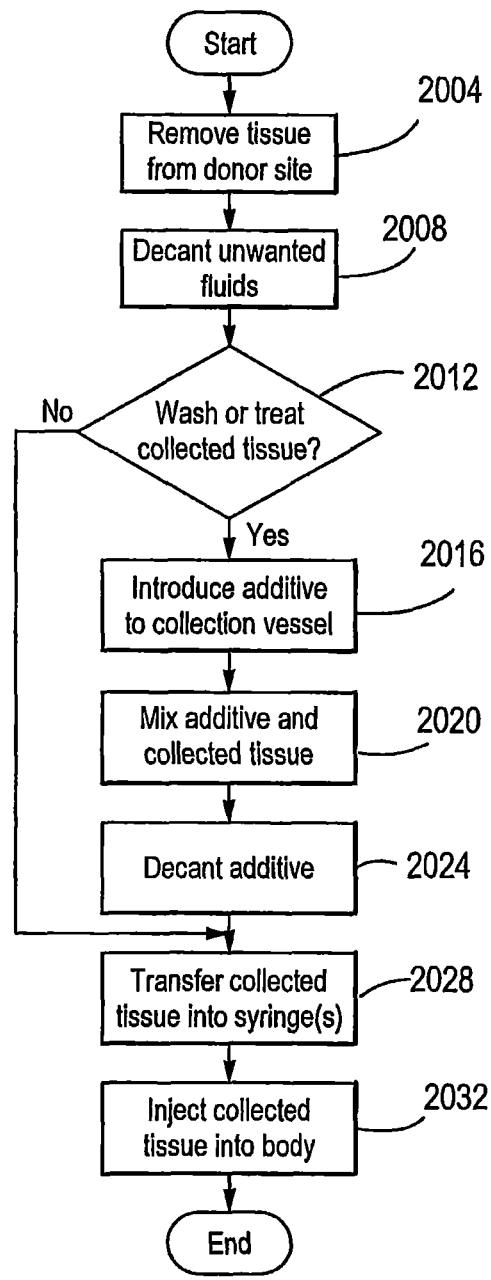
FIG. 20 is a flowchart depicting aspects of the operation of a device for collecting tissue in accordance with other embodiments of the present invention.

FIG. 20 is a flowchart illustrating aspects of the operation of a device for collecting tissue 1504 that utilizes a collection bag 1904. Initially, at step 2004, tissue is removed from a donor site using a vacuum applied through the cannula 118 and the intermediate tubing 1016, and the removed tissue is deposited into the collection bag 1904. At step 2008, unwanted fluids are decanted or removed from the collection bag 1904. This can include removing the collection bag 1904 from the canister 1508, disconnecting the bag from the seal assembly 1924 (and then disconnecting the bag 1904 from the cannula 118 and the vacuum source 1548), and turning the bag such that the ports 1908, and 1912 are lower than the material collected in the bag 1904. One of the ports 1908, 1912 can then be opened, to allow fluid collected at the bottom of the collection bag 1904 to drain out of the bag, separating that fluid from tissue comprising collected fat cells.

At step 2012, a determination is made as to whether the remaining collected tissue should be washed or treated. If the collected tissue is to be washed or treated, an additive can be introduced to the interior of the collection vessel 1904 though one of the ports 1904, 1912 (step 2016). The additive and collected tissue may then be mixed together (step 2020). Mixing the additive and the collected tissue can comprise massaging the exterior of the collection bag 1904, to ensure complete mixing of the additive and collected tissue. At step 2024, the additive can be decanted from the bag. After decanting the additive, or after determining that washing or treatment of collected tissue will not be performed, the collected tissue is transferred into one or more syringe bodies 1516 (step 2028). In accordance with embodiments of the present invention, transferring collected tissue into a syringe body 1516 can include removing or forcing tissue through a port 1904, 1912 and into the body 1516 of a syringe, either directly or through a piece of intermediate tubing. In accordance with still other embodiments of the present invention, transferring collected tissue into syringes can include removing the collected tissue from the tissue collection bag 1904, and passing that tissue to a tissue collection device 1504 comprising a plurality of syringe bodies 1516. Accordingly, a tissue collection device 1504 may comprise multiple stages, with a first stage comprising a tissue collection bag 1904, as described in connection with FIG. 19A or B, and a second stage comprising a plurality of syringe bodies 1516, as described in connection with FIGS. 15 and 16, to facilitate the loading of tissue in the syringe bodies 1516 for reinjection. The collected tissue can then be injected into an injection site (step 2032).

In accordance with embodiments of the present invention, a canister 1508 may comprise a polycarbonate canister with an integrated bracket 1552 and vacuum outlet 1544. The size of the canister may vary. For example, the canister 1508 may have a capacity of from 100 to 5,000 cc's. In accordance with other embodiments, the canister 1508 may have a capacity of 3,000 cc's. As an alternative to polycarbonate, the canister 1508 may be formed from any polymer, metal or glass. Moreover, because the canister 1508 is not typically in contact with harvested fat, it does not need to be made from an FDA approved resin. However, it is desirable to provide a canister 1508 that is autoclavible, so that syringe bodies 1516, collection bags 1904, or other components can be changed under sterile conditions. The syringe bodies 1516 may be any syringe body suitable for use in connection with the injection of tissue or compounds into a body. The syringe bodies 1516 may have any capacity. For example, the syringe bodies 1516 may have capacities of from about 1 cc to about 100 cc. In accordance with other embodiments of the present invention, the syringe bodies 1516 may have a capacity of 60 cc's. In accordance with still other embodiments of the present invention, the syringe bodies 1516 can have holes or perforations in order to function as a filter. Accordingly, the syringe bodies 1516 may comprise an inner chamber 112 as described elsewhere herein.

A collection bag 1904 may comprise a bag that is FDA approved for containing blood or other fluids intended for injection into a human or animal body. The capacity of a collection bag 1904 may vary. For example, the collection bag 1904 may have a capacity of from 100 to 2,000 cc's. Commonly available bags have three ports. If such a bag is used as a collection bag 1904, a first port may be used as the intake port 1908, the second port may be used as the vacuum outlet port 1912, and the third port may be capped or plugged. If desired, any one of the ports may be provided with a valve, for example to assist in decanting or removing unwanted fluids or introducing additives. As an alternative to a collection bag 1904, a collection vessel 1514 may comprise a rigid container. Because of the vacuum produced in the interior of the canister 1508, the walls of the collection vessel can be less resistant to collapse than if the collection vessel was used in atmospheric pressure.

If provided, a filter or filter bag 1916 is generally used to separate desired tissue from undesired fluids or cells. For example, where the desired tissue comprises tissue that will be used for reinjection, the pores of the filter or filter bag 1916 may be about 500 microns, plus or minus 200 microns, to retain parcels of fat cells, and to allow fluids and undesirable fat cells to pass through the filter.

Figure 21:
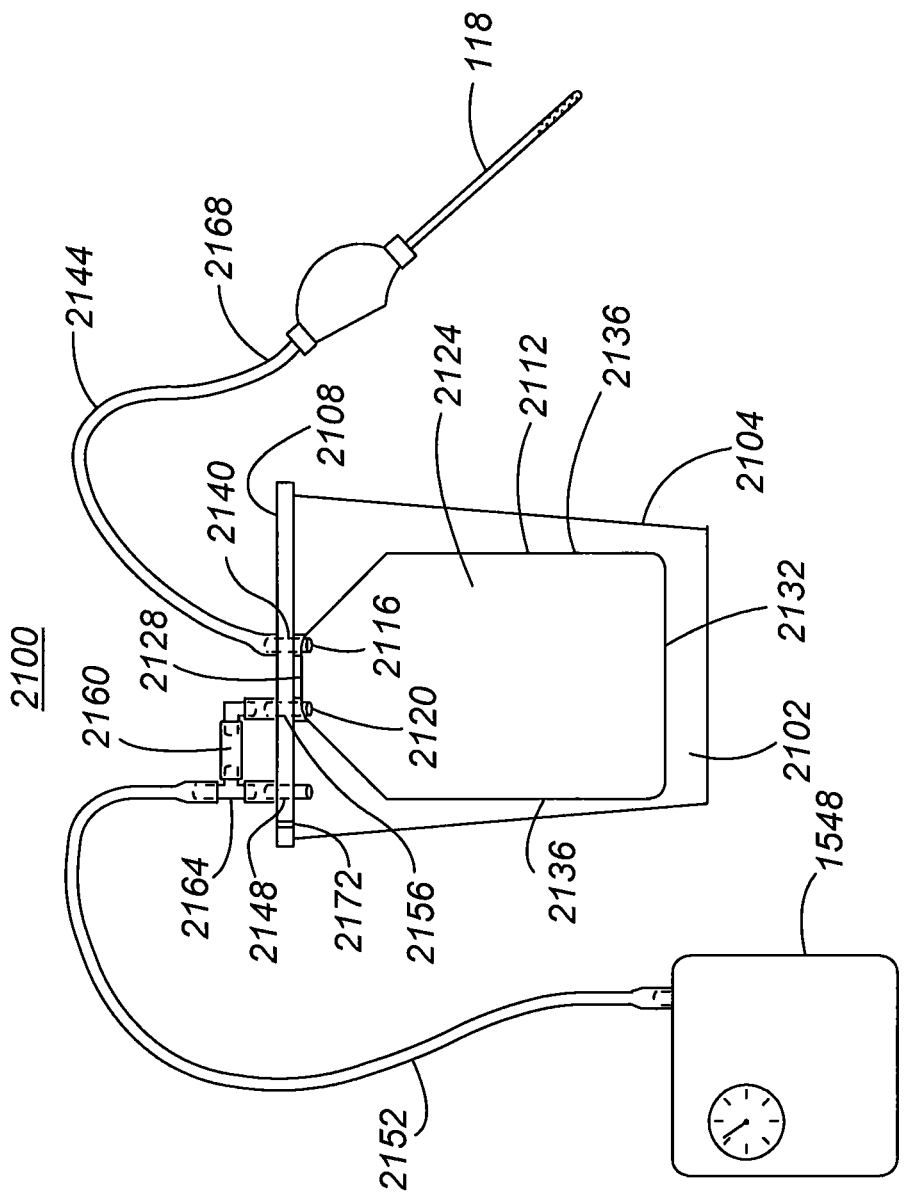
FIG. 21 depicts a tissue transfer system in accordance with embodiments of the present invention.

FIG. 21 illustrates a tissue collection system 2100 in accordance with embodiments of the present invention. The tissue collection system 2100 generally includes a tissue collection canister 2104 with a canister lid 2108. When the lid 2108 is fitted to the canister 2104, the interior volume of the canister 2104 is sealed, except for various inlets and ports as will be described in detail herein. In accordance with embodiments of the present invention, the canister 2104 is rigid, to define an essentially constant interior volume.

Within the interior volume of the canister 2104 is a tissue collection vessel 2112. The tissue collection vessel 2112 may comprise an impermeable bag formed from a flexible material. Alternatively, the tissue collection vessel 2112 may comprise a rigid or semi-rigid container. The tissue collection vessel 2112 generally includes an inlet 2116 and an outlet 2120. In addition, in accordance with embodiments of the present invention, the width of a collection volume 2124 defined by the tissue collection vessel 2112 is less along a first edge 2128 that includes at least one of the inlet 2116 and the outlet 2120 then along a second edge 2132 opposite the first edge 2128. For example, the sides 2136 of the tissue collection vessel 2112 may be tapered at or towards the first edge 2128. In accordance with still other embodiments, the tissue collection volume 2112 may feature a conical section that narrows towards the first edge 2128. In accordance with further embodiments of the present invention, the first edge 2128 may have a length that is less than one half the length of the second edge 2132.

The lid 2108 of the tissue collection canister 2104 may feature a plurality of ports. For example, a first port 2140 may be provided to place the inlet 2116 of the tissue collection vessel 2112 in communication with a length of harvest tubing 2144 that is in turn interconnected to a tissue collection cannula 118. A second port 2148 may be provided that places the interior volume 2102 of the tissue collection canister 2104 in communication with a vacuum source 1548 via a length of vacuum tubing 2152. A third port 2156 may be provided to place the interior volume 2124 of the tissue collection vessel 2112 in communication with the vacuum source 1548 via the length of vacuum tubing 2152 at the outlet port 2120 of the tissue collection vessel 2112.

In accordance with embodiments of the present invention, the volume of tubing, including the vacuum tubing 2152 interconnecting the vacuum source 1548 to the third port 2156 is greater than the volume of tubing including the vacuum tubing 2152 interconnecting the vacuum source 1548 to the second port 2148. For example, an additional section of vacuum tubing or an extension section 2160 that extends from a T-fitting 2164 proximate to the second port 2148 is provided to place the third port 2156 in communication with the vacuum source 1548. As a result, the vacuum potential at the second port 2148 is greater than at the third port 2156. Therefore, a vacuum may be introduced in the interior volume 2124 of the tissue collection vessel 2112, and a greater vacuum can be introduced in the interior volume 2102 of the tissue collection canister 2104 about an exterior of the tissue collection vessel 2112, to maintain the tissue collection vessel 2112 in an open or inflated configuration, to facilitate the deposition of collected tissue into the tissue collection vessel 2112.

The inlet 2116 to the tissue collection vessel 2112 is preferably located at some distance from the outlet 2120 of the tissue collection vessel 2112. For example, the distance between the inlet 2116 and the outlet 2120 may be at least 1.5 inches. This spacing can reduce or eliminate the tendency for collected tissue to be sucked into the outlet 2120, instead of being deposited into and held by the tissue collection vessel 2112.

An air inlet hole 2168 may be formed in the harvest tubing 2144. The provision of an air inlet 2168 allows ambient air to be admitted into the harvest tubing 2144, to provide a cushion for fat cells being transported from the cannula 118 to the tissue collection vessel 2112. This is believed to protect the fat cells from damage and to facilitate the flow of harvested tissue, including harvested fat cells, along the harvest tubing 2144.

Alternatively or in addition, an air inlet 2172 may be provided in one or more of the walls defining the interior volume of the tissue collection canister 2104. For example, an air inlet 2172 may be provided in the tissue collection canister lid 2108. The inclusion of an air inlet 2172 in the tissue collection canister 2104 can reduce the vacuum within the tissue collection canister 2104 relative to the ambient environment. By thus limiting the vacuum formed within the tissue collection canister 2104, the risk of implosion of the tissue collection canister 2104 is reduced.

In accordance with further embodiments of the present invention, various surfaces of the system 2100 are coated in silicone. For example, by coating surfaces such as the interior of the harvest tubing 2144 or the interior of the tissue collection vessel 2112, materials that are not approved by the Federal Drug Administration (FDA) for transporting or holding collected tissue prior to reinjection can be used for the harvest tubing 2144 and/or the tissue collection vessel 2112. Coating such surfaces in silicone can also reduce surface imperfections, so that a smoother surface is presented to collected tissue. By providing a smoother surface, damage to collected fat cells can be reduced, and the transport of tissue can be facilitated.

Figure 22:
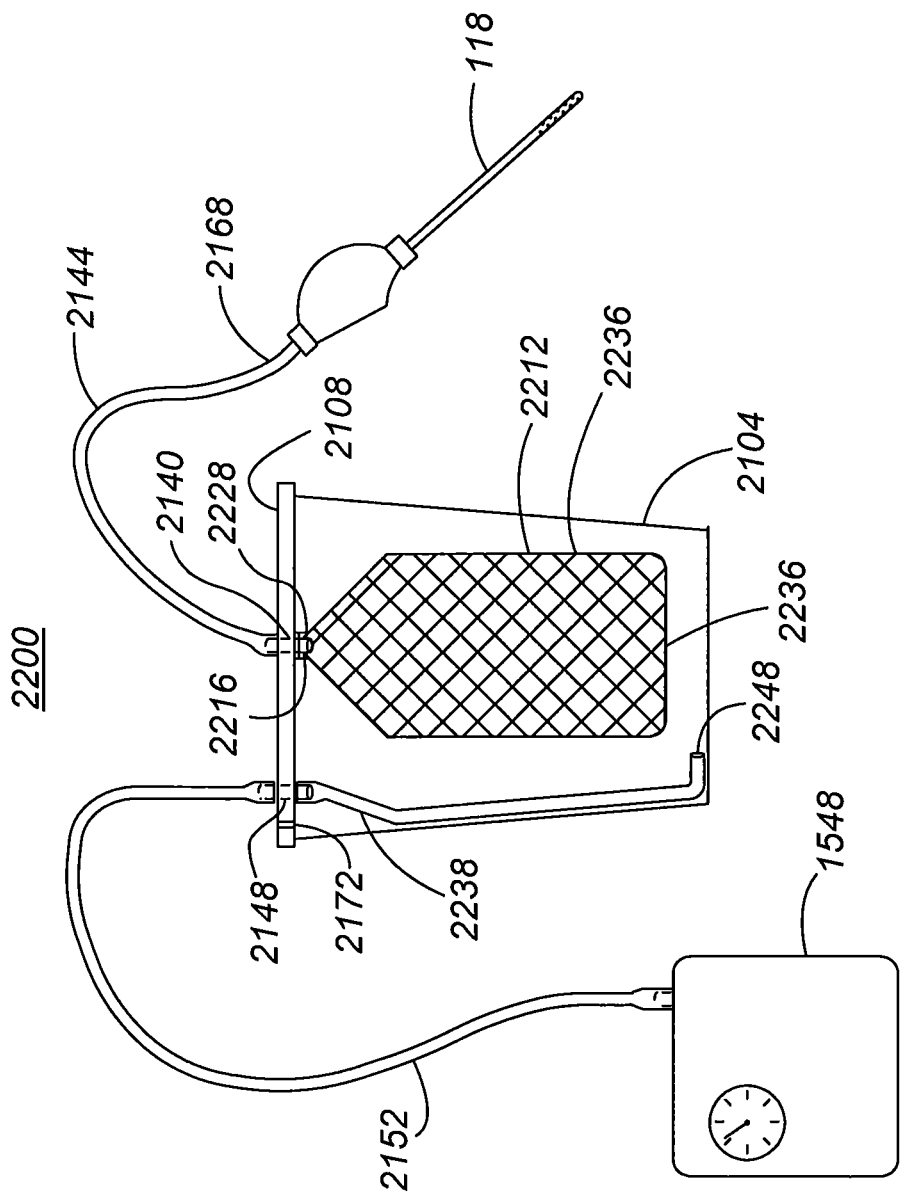
FIG. 22 depicts a tissue transfer system in accordance with other embodiments of the present invention.

FIG. 22 illustrates a tissue collection system 2200 in accordance with other embodiments of the present invention. The tissue collection system 2200 includes a tissue collection vessel 2212 having a permeable section or sections. More particularly, the tissue collection vessel 2212 may comprise a material with holes sized such that liquids can pass through the walls of the tissue collection vessel 2212, while fat cells are retained within the interior volume of the tissue collection vessel 2212. For example, the tissue collection vessel 2212 walls have holes that are less than or equal to 800 µm. As with other embodiments, the tissue collection vessel 2212 may feature side walls 2236 that taper towards a first end 2228. An inlet 2216 in the tissue collection vessel 2212 admits tissue collected by the cannula 118. Because the walls of the tissue collection vessel 2212 are permeable, a separate outlet is not required. The inlet 2216 may be interconnected to harvest tubing 2144 via a first port 2140 in the lid 2108 of the tissue collection canister 2104.

A length of waste tubing 2238 may be connected to vacuum tubing 2152 and in turn to a vacuum source 1548 via a second port 2148 in the collection canister lid 2108. The inlet 2248 to the waste tubing 2238 may be placed at or proximate to the bottom of the tissue collection canister 2104 when the system 2200 is in use. Accordingly, the waste tubing 2238 may introduce a vacuum into the interior volume of the tissue collection canister 2104, and may also remove fluids that have passed through the walls of the tissue collection vessel 2212.

The system 2200 may include an air inlet 2168 in the harvest tubing to cushion the transport of fat cells along the harvest tubing 2168 and to improve this transport of fat along the harvest tubing 2144. Alternatively or in addition, an air inlet 2172 may be formed in the tissue collection canister 2104, for example in the tissue collection canister lid 2108, to reduce the relative vacuum formed within the tissue collection canister 2104.

Figure 23:
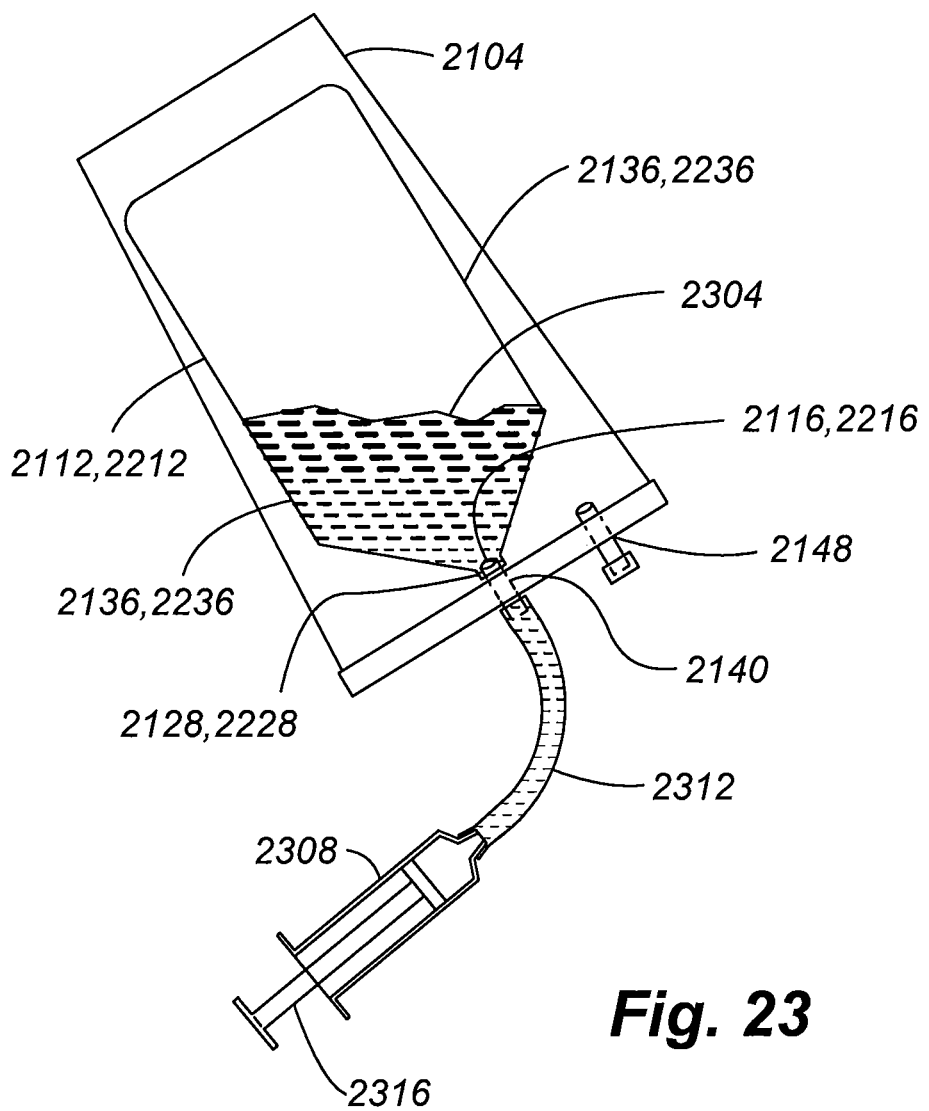
FIG. 23 depicts the removal of collected tissue from a tissue collection vessel in accordance with embodiments of the present invention.

In FIG. 23, the removal of collected tissue 2304 from a tissue collection vessel 2112, 2212 is illustrated. In general, the removal includes capping or otherwise closing all but one of the ports in the canister lid 2108 (e.g., by capping the second 2148 port and (if provided) the third port 2156) and inverting the tissue collection canister 2104 so that collected tissue 2304 is displaced towards the first edge 2128, 2228 of the tissue collection vessel 2112, 2212. In addition, where the sides 2136, 2236 of the tissue collection vessel 2112, 2212 are tapered towards the first edge 2128, 2228, the collected tissue 2304 is concentrated towards the inlet 2116, 2216. The first port 2140 of the tissue collection canister 2104 is interconnected to a syringe 2308 by a length of tubing 2312. Collected tissue 2304 can be drawn into the body of the syringe 2308 by pulling back the plunger 2316 of the syringe 2308 after the tissue 2304 has been displaced towards the inlet 2116, 2216 of the tissue collection vessel 2112, 2212. Accordingly, it can be appreciated that the tapered sides 2136, 2236 facilitates the removal of collected tissue 2304 from the tissue collection vessel 2112, 2212 to a syringe 2308 for reinjection.

Figure 24:
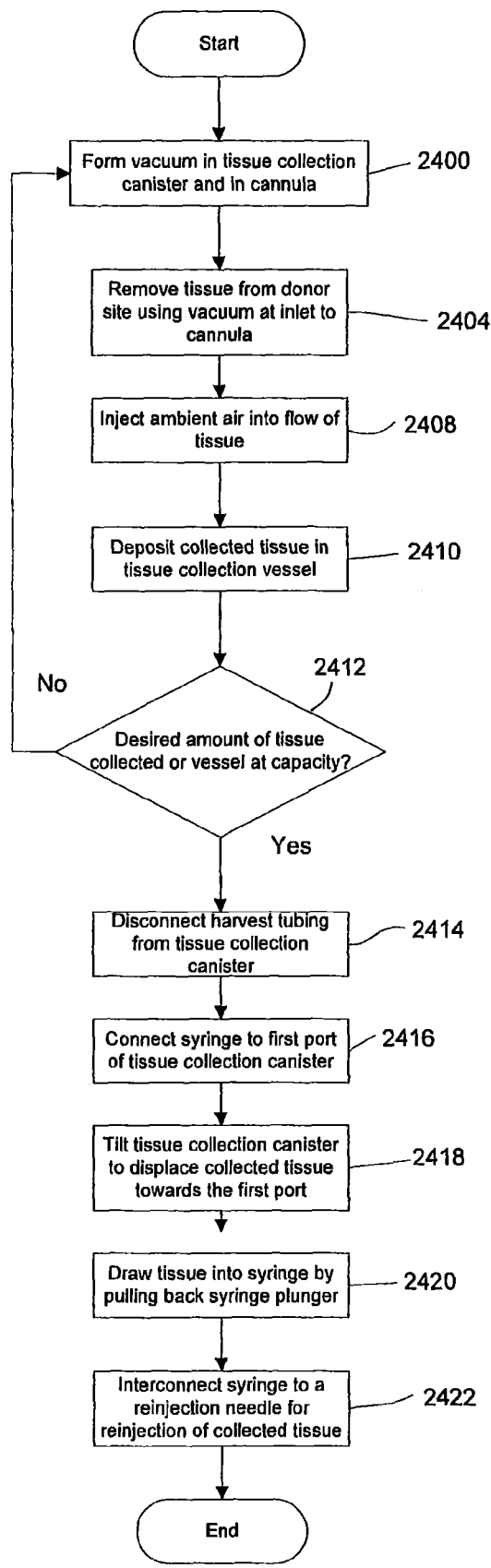
FIG. 24 is a flowchart illustrating aspects of a method for transferring tissue in accordance with embodiments of the present invention.

FIG. 24 illustrates aspects of a method for tissue transfer in accordance with embodiments of the present invention. Initially, at step 2400, a vacuum is formed in a tissue collection canister 2104 and in a cannula 118 interconnected to the tissue collection canister 2104. In accordance with embodiments of the present invention, air is admitted into the interior of the tissue collection canister 2104 through an air inlet 2172. At step 2404, tissue is removed from a donor site using a vacuum applied at an inlet to a cannula 118. At step 2408, ambient air is injected into the flow of tissue through an air inlet 2168 formed in harvest tubing 2144. At step 2410, tissue is deposited into the tissue collection vessel 2112, 2212.

At step 2412, a determination is made as to whether a desired amount of tissue has been collected, or whether the tissue collection vessel 2112, 2212 is at capacity. If additional tissue is to be collected, the process may return to step 2400. If a desired amount of tissue has been collected, the harvest tubing 2144 can be disconnected from the first port 2140 of the tissue collection canister 2104 (step 2414). Next, a syringe 2308 can be connected to the first port 2140 by a length of tubing 2312 (step 2416). Alternatively, the port or tip of the syringe can be connected to the first port 2140. At step 2418, the tissue collection canister 2104 can be tilted or inverted so that collected tissue 2304 is displaced towards the first port 2140 of the tissue collection canister 2104. In accordance with embodiments of the present invention, tapered side walls 2136, 2236 concentrate the collected tissue 2304 around the first port 2120 when the tissue collection canister 2104 and the tissue collection vessel 2112, 2212 within a canister 2104 are inverted. At step 2420, the collected tissue 2304 is drawn into the syringe 2308 by pulling back the plunger 2316 of the syringe 2308. At step 2422, the syringe 2308 can be interconnected to a reinjection needle, and the collected tissue 2304 can be reinjected into a body. The process may then end.

The foregoing discussion of the invention has been presented for purposes of illustration and description. Further, the description is not intended to limit the invention to the form disclosed herein. Consequently, variations and modifications commensurate with the above teachings, within the skill or knowledge of the relevant art, are within the scope of the present invention. The embodiments described hereinabove are further intended to explain the best mode presently known of practicing the invention and to enable others skilled in the art to utilize the invention in such or in other embodiments and with the various modifications required by their particular application or use of the invention. It is intended that the appended claims be construed to include alternative embodiments to the extent permitted by the prior art.

What is claimed is:

1. A tissue transfer system, comprising:
a tissue collection canister;
a tissue collection canister lid, the tissue collection canister lid including a first port, a second port, and a third port;
a tissue collection vessel within the tissue collection canister, wherein the tissue collection vessel is impermeable, and wherein the third port of the tissue collection canister lid is in communication with an interior of the tissue collection vessel through an outlet of the tissue collection vessel;
harvest tubing, wherein a first end of the harvest tubing is interconnected to an inlet of the tissue collection vessel via the first port of the tissue collection canister lid;
a tissue collection cannula interconnected to a second end of the harvest tubing, wherein the tissue collection cannula is in communication with an interior of the tissue collection vessel via the harvest tubing, the first port of the tissue collection canister lid, and the inlet of the tissue collection vessel;
a vacuum source;
vacuum tubing, wherein via the vacuum tubing an interior of the tissue collection canister is in communication with the vacuum source, the second port of the tissue collection canister lid, and the third port of the tissue collection canister lid, wherein the second port of the tissue collection canister lid is also in communication with an interior of the tissue collection canister and an exterior of the tissue collection vessel.

2. The system of claim 1, wherein the vacuum tubing interconnects the second and third ports of the tissue collection canister lid, and wherein the third port is in communication with the second port and the vacuum tubing via a tee fitting.

3. The system of claim 2, wherein a volume of tubing between the third port of the collection canister lid and the vacuum source is greater than a volume of tubing between the second port of the collection canister lid and the vacuum source.

4. The system of claim 1, wherein the second port of the tissue collection canister lid is connected to a waste tube.

5. The system of claim 4, wherein an inlet to the waste tube is located at an end of the tissue collection canister opposite the tissue collection canister lid.

6. The system of claim 1, further comprising:
an air inlet in at least one of the harvest tubing and the tissue collection canister.

7. The system of claim 1, wherein the tissue collection canister lid includes a first air inlet.

8. The system of claim 1, wherein an end of the tissue collection vessel proximate to the inlet of the tissue collection vessel is tapered.

9. The system of claim 1, further comprising:
a silicone coating on at least one of an interior of the tissue collection canister and an interior of the harvest tubing.

10. The system of claim 1, wherein a length along a first edge of the tissue collection vessel at an end proximate to the inlet is less than one half a length along a second edge of the tissue collection at an end distal from the inlet.

11. A tissue collection device, comprising:
a tissue collection canister, including:
a first port;
a second port;
a third port;
an impermeable tissue collection vessel, wherein an interior of the tissue collection vessel is in communication with the first port of the tissue collection canister, wherein the first port of the tissue collection canister is located at a first end of the tissue collection canister, wherein the first port of the tissue collection canister is in communication with an interior of the tissue collection vessel through an inlet to the interior of the tissue collection vessel, wherein the second port of the tissue collection canister is located at the first end of the tissue collection canister, wherein the second port of the tissue collection canister is in communication with an interior of the tissue collection canister and an exterior of the tissue collection vessel, wherein the third port of the tissue collection canister is located at the first end of the tissue collection canister, wherein the third port of the tissue collection canister is in communication with the interior of the tissue collection vessel through an outlet of the tissue collection vessel, and wherein the second and third ports of the tissue collection canister are in communication with each other.

12. The device of claim 11, wherein a first end of the tissue collection vessel is tapered in at least one of width and depth.

13. The device of claim 11, wherein the tissue collection canister includes an air inlet.

14. The device of claim 11, wherein the second and third ports are in communication with each other through a common vacuum line.

15. The device of claim 14, wherein the common vacuum line is vacuum tubing.

* * * * *